(12) United States Patent
Polinsky

(10) Patent No.: US 10,099,086 B2
(45) Date of Patent: Oct. 16, 2018

(54) BALANCE BOARD FITNESS TRAINING DEVICE

(71) Applicant: Nautilus, Inc., Vancouver, WA (US)

(72) Inventor: Glenn Polinsky, Waunakee, WI (US)

(73) Assignee: Nautilus, Inc., Vancouver, WA (US)

( * ) Notice: Subject to any disclaimer, the term of this patent is extended or adjusted under 35 U.S.C. 154(b) by 0 days.

(21) Appl. No.: 14/975,276

(22) Filed: Dec. 18, 2015

(65) Prior Publication Data
US 2017/0043219 A1 Feb. 16, 2017

Related U.S. Application Data

(60) Provisional application No. 62/203,851, filed on Aug. 11, 2015.

(51) Int. Cl.
*A63B 26/00* (2006.01)
*A63B 71/06* (2006.01)
(Continued)

(52) U.S. Cl.
CPC .......... *A63B 26/003* (2013.01); *A61B 5/1118* (2013.01); *A63B 21/0004* (2013.01); *A63B 21/068* (2013.01); *A63B 22/18* (2013.01); *A63B 22/20* (2013.01); *A63B 23/0211* (2013.01); *A63B 23/0222* (2013.01); *A63B 23/03525* (2013.01); *A63B 71/0622* (2013.01);
(Continued)

(58) Field of Classification Search
CPC ............ A63B 24/0052; A63B 24/0065; A63B 24/0068; A63B 24/0071; A63B 69/0093; A63B 2220/00–2220/80
See application file for complete search history.

(56) References Cited

U.S. PATENT DOCUMENTS 87,831 A * 3/1869 Farmer ............... B62B 1/24
298/2
616,746 A 12/1898 Taylor
(Continued)

FOREIGN PATENT DOCUMENTS

KR 20130022628 A 3/2013
WO 2016183384 A1 11/2016

OTHER PUBLICATIONS

"Lifeline Power Wheel", http://www.lifelinefitness.com/store/products/ProductDetail.php?ProductID=685, available as early as Aug. 10, 2015.
(Continued)

*Primary Examiner* — Loan H Thanh
*Assistant Examiner* — Rae Fischer
(74) *Attorney, Agent, or Firm* — Dorsey & Whitney LLP

(57) ABSTRACT

A balance board fitness training device is provided. The fitness training device may include a deck having a top surface, a bottom surface, and opposing first and second side edges and opposing front and rear longitudinal edges together forming a perimeter of the deck; at least one wheel bracket structure positioned below the deck, the at least one wheel bracket structure rotatably supporting at least two wheels and configured so as to be movable relative to the deck about a pivot line at least partially extending between the opposing first and second side edges of the deck; and at least one resilient damping member connected to the at least one wheel bracket structure and the deck.

23 Claims, 24 Drawing Sheets

(51) Int. Cl.

| | |
|---|---|
| A63B 21/00 | (2006.01) |
| A63B 21/068 | (2006.01) |
| A63B 22/18 | (2006.01) |
| A63B 22/20 | (2006.01) |
| A63B 23/02 | (2006.01) |
| A63B 23/035 | (2006.01) |
| G06F 19/00 | (2018.01) |
| G06Q 50/00 | (2012.01) |
| G09B 19/00 | (2006.01) |
| A61B 5/11 | (2006.01) |
| A63F 13/245 | (2014.01) |
| A63B 65/06 | (2006.01) |
| A63B 69/00 | (2006.01) |
| A63B 69/18 | (2006.01) |
| A63B 71/00 | (2006.01) |
| A63B 22/16 | (2006.01) |
| A63B 23/04 | (2006.01) |
| A63B 23/12 | (2006.01) |
| A63B 21/015 | (2006.01) |
| A63B 21/02 | (2006.01) |
| A63B 21/072 | (2006.01) |

(52) U.S. Cl.
CPC ........ *A63F 13/245* (2014.09); *G06F 19/3481* (2013.01); *G06Q 50/01* (2013.01); *G09B 19/0038* (2013.01); *A63B 21/00069* (2013.01); *A63B 21/015* (2013.01); *A63B 21/023* (2013.01); *A63B 21/026* (2013.01); *A63B 21/0726* (2013.01); *A63B 21/4034* (2015.10); *A63B 21/4035* (2015.10); *A63B 22/16* (2013.01); *A63B 23/03541* (2013.01); *A63B 23/0405* (2013.01); *A63B 23/0488* (2013.01); *A63B 23/1236* (2013.01); *A63B 65/06* (2013.01); *A63B 69/0022* (2013.01); *A63B 69/18* (2013.01); *A63B 71/0054* (2013.01); *A63B 2071/065* (2013.01); *A63B 2071/0625* (2013.01); *A63B 2071/0638* (2013.01); *A63B 2071/0658* (2013.01); *A63B 2208/0204* (2013.01); *A63B 2208/0214* (2013.01); *A63B 2208/0219* (2013.01); *A63B 2208/0242* (2013.01); *A63B 2208/0295* (2013.01); *A63B 2209/02* (2013.01); *A63B 2210/50* (2013.01); *A63B 2220/12* (2013.01); *A63B 2220/20* (2013.01); *A63B 2220/30* (2013.01); *A63B 2220/40* (2013.01); *A63B 2220/803* (2013.01); *A63B 2225/20* (2013.01); *A63B 2225/50* (2013.01); *A63B 2230/75* (2013.01)

(56) References Cited

U.S. PATENT DOCUMENTS

| | | | |
|---|---|---|---|
| D31,802 S | 11/1899 | Gardner | |
| RE22,749 E | 4/1946 | Mason | |
| 2,398,436 A | 4/1946 | Mason | |
| 2,508,812 A | 5/1950 | Burger | |
| 3,522,953 A | 8/1970 | Gold | |
| 4,181,319 A * | 1/1980 | Hirbod | A63C 17/12 280/11.115 |
| 4,230,330 A * | 10/1980 | Muhammad | A63C 17/01 280/87.042 |
| 5,201,659 A | 4/1993 | Nelson | |
| 5,263,725 A | 11/1993 | Gesmer et al. | |
| D373,400 S | 9/1996 | Ogata et al. | |
| 6,019,382 A | 2/2000 | Bouden | |
| 6,267,394 B1 | 7/2001 | Bouden | |
| 6,428,022 B1 | 8/2002 | Namiki | |
| D464,389 S | 10/2002 | Schouten et al. | |
| 6,698,776 B2 | 3/2004 | Todd | |
| 6,764,082 B2 * | 7/2004 | Roderick | A43B 5/005 280/11.19 |
| D498,810 S | 11/2004 | Stanisewski, Jr. | |
| D513,425 S | 1/2006 | Kohl | |
| D567,318 S | 4/2008 | Farrelly et al. | |
| D572,332 S | 7/2008 | Sramek et al. | |
| D649,595 S | 11/2011 | Marcus | |
| 8,308,171 B2 | 11/2012 | Farrelly | |
| 8,500,146 B2 | 8/2013 | Genov et al. | |
| D699,803 S | 2/2014 | Yamabe | |
| D724,166 S | 3/2015 | Hamborg et al. | |
| D741,431 S | 10/2015 | Wells | |
| D770,585 S | 11/2016 | Desberg | |
| D797,212 S | 9/2017 | Polinsky | |
| 2002/0011713 A1 | 1/2002 | Kirkland | |
| 2002/0163144 A1 | 11/2002 | Guerra | |
| 2008/0092338 A1 | 4/2008 | Wu | |
| 2010/0090423 A1 | 4/2010 | Farrelly | |
| 2012/0116714 A1 * | 5/2012 | Rogel | H04R 1/02 702/150 |
| 2012/0223493 A1 | 9/2012 | Cortez | |
| 2013/0296147 A1 | 11/2013 | Cruz | |
| 2016/0089576 A1 | 3/2016 | Rosenstiel | |
| 2016/0250513 A1 | 9/2016 | Ho et al. | |

OTHER PUBLICATIONS

"Roll-Board by Modern Movement", http://www.modmov.com/products/roll-board, available as early as Aug. 10, 2015.

"Valeo VA2413RE Dual Ab Wheel—Black/Red", http://www.amazon.com/Valeo-VA2413RE-Dual-Ab-Wheel/dp/B0113Y4RAK; available as early as Aug. 10, 2015.

"Valslide Pads", http://www.valslide.com, available as early as Aug. 10, 2015.

\* cited by examiner

BALANCE BOARD FITNESS TRAINING DEVICE

CROSS-REFERENCE TO RELATED APPLICATIONS

This application claims the benefit of priority under 35 U.S.C. 119(e) of U.S. provisional patent application No. 62/203,851 filed 11 Aug. 2015 entitled "Hardware and software for roller board fitness training device," which is hereby incorporated herein in its entirety.

TECHNICAL FIELD

The present disclosure relates generally to physical fitness and personal training and more specifically to devices and systems for balance training.

BACKGROUND

Various devices and systems exist to perform a variety of fitness and balance training exercises. These devices and systems, however, do not provide sufficient selective control by the user, user feedback, and/or user tracking.

It is therefore desirable to provide an improved fitness and balance training device that addresses at least in part the above-identified issues and/or which more generally offers improvements or an alternative to existing arrangements.

SUMMARY

Described herein is a fitness training device and system. In some embodiments, the fitness training system may include a sensing device, training software, and/or a secondary display. The fitness training device may be compact and portable. A broad range of exercises, such as lunges, abdominal extensions, atomic pushups, hamstring curls, reptilian crawls, pike ups, and others, may be performed using the fitness training device. The training software may demonstrate exercise movements and may guide a user through the workout. The training software may leverage sensors associated with the sensing device, such as a smartphone or other suitable device, to track the movements and provide feedback, allowing a user to review the user's ability and improvement over time.

Embodiments of the present disclosure may include a fitness training device. The fitness training device may include a deck, at least one wheel bracket structure positioned below the deck, and at least one resilient damping member connected to the at least one wheel bracket structure and the deck. The deck may include a top surface, a bottom surface, and opposing first and second side edges and opposing front and rear longitudinal edges together forming a perimeter of the deck. The at least one wheel bracket structure may rotatably support at least two wheels and may be configured so as to be movable relative to the deck about a pivot line at least partially extending between the opposing first and second side edges of the deck.

In some embodiments, the at least two wheels may be positioned to rotate about an axis parallel to the pivot line.

In some embodiments, each of the at least two wheels may be a roller including a diameter less than a length. The diameter of each of the at least two wheels may increase from opposing ends of each wheel towards a mid-point of each wheel. Each of the at least two wheels may include a barrel-shape. Each of the at least two wheels may be positioned so that at least 50% of the diameter is within the perimeter of the deck. In some embodiments, approximately 100% of the diameter may be within the perimeter of the deck.

In some embodiments, the deck may include a channel extending at least partially along the bottom surface between the opposing first and second longitudinal side ends. The at least one wheel bracket structure may include a securement structure. A joint may be formed by the securement structure positioned within the channel and defining the pivot line, the joint accommodating relative movement between the deck and the at least one wheel bracket structure. In some embodiments, the relative movement between the deck and the wheel bracket structure may be resisted or dampened by the at least one resilient damping members. In some embodiments, the channel may be C-shaped and may include first and second troughs and a rib having a convex lower surface. The securement structure may be C-shaped and may include a first portion and a second portion, the second portion having a concave upper surface. The concave upper surface of the securement structure may engage the convex lower surface of the rib to define the pivot line. In some embodiments, the second portion of the securement structure may include opposing arms extending away from each other. The opposing arms may be each received in an adjacent one of the first and second troughs. In some embodiments, the channel may define a gap including a first width dimension, the opposing arms may define a second width dimension, and the first width dimension may be less than the second width dimension to retain the second portion of the securement structure within the channel.

In some embodiments, the at least one wheel bracket structure may include at least two wheel brackets. Each wheel bracket may be positioned adjacent one of the opposing first and second side edges and perpendicular to a width of the deck. In some embodiments, the deck may include at least one channel extending along the bottom surface between the opposing first and second longitudinal side ends. Each wheel bracket may include a securement structure. A joint may be formed by an engagement of the securement structure on each wheel bracket and a corresponding one of the at least one channel, each joint defining a common pivot line, the joint accommodating relative movement between the deck and the wheel bracket structure. In some embodiments, the relative movement between the deck and the wheel bracket structure may be resisted or dampened by the at least one resilient damping members.

In some embodiments, the bottom surface may include at least one recess portion sized for at least partial receipt of a peripheral portion of at least one of the at least two wheels. Relative movement between the deck and the at least one wheel bracket structure may cause contact between the at least one recess portion and a peripheral portion of the at least one of the at least two wheels to create a braking action.

In some embodiments, a deck pad may be positioned on the top surface of the deck. The deck pad may include depressions to provide tactile feedback for feet of a user to be quickly placed in a correct location.

In some embodiments, the materials and shapes of the top surface of the deck may be appropriate for hands of a user to be comfortably supported during exercises.

In some embodiments, the at least two wheels may be barrel-shaped to allow the deck to rock slightly along a length of the deck.

In some embodiments, the at least two wheels may be barrel-shaped to allow the deck to move in broad arcing turns.

In some embodiments, the deck may create a braking action when angled slightly towards and contacting at least one of the at least two wheels mounted in the at least one wheel bracket structure.

In some embodiments, the at least one damping member may be operable to maintain the top surface of the deck substantially parallel to a support surface, and may provide a resilient force when a user engages in an off-center, angled load on the deck with reference to a side plane.

In some embodiments, the at least two wheels may be positioned so as to not extend beyond a peripheral edge of the deck.

Embodiments of the present disclosure may include a system including a fitness training device. The system may include a sensing device including a plurality of sensors and data transmission means, a software provided on the sensing device, and a secondary display. The software may enable periodic reading of the plurality of sensors to provide feedback to a user during workout. The software may instruct the sensing device to transmit data to the secondary display via the data transmission means.

Additional embodiments and features are set forth in part in the description that follows, and will become apparent to those skilled in the art upon examination of the specification or may be learned by the practice of the disclosed subject matter. A further understanding of the nature and advantages of the present disclosure may be realized by reference to the remaining portions of the specification and the drawings. One of skill in the art will understand that each of the various aspects and features of the present disclosure may advantageously be used separately in some instances, or in combination with other aspects and features of the disclosure in other instances.

BRIEF DESCRIPTION OF THE DRAWINGS

Various examples of embodiments of the systems and methods according to the present disclosure will be described in detail, with reference to the following figures, wherein.

Figure 1:
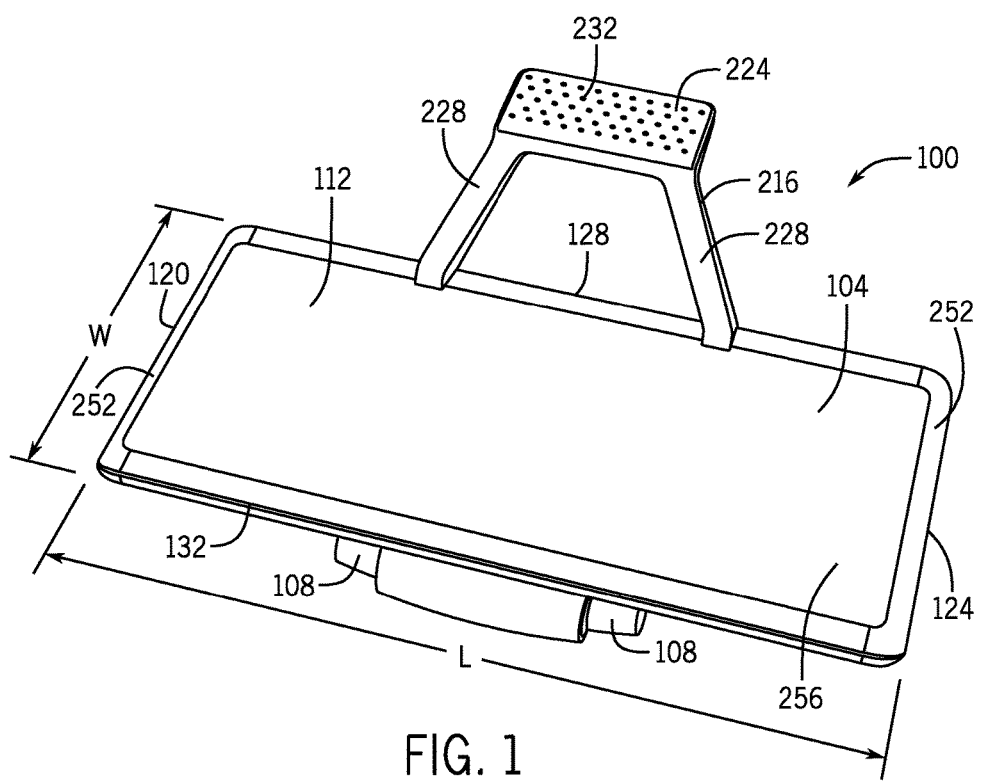
FIG. 1 is a perspective view of an embodiment of a fitness training device, with a phone bracket attachment.

The drawings are not necessarily to scale. In certain instances, details that are unnecessary to understanding the subject matter or render other details difficult to perceive may have been omitted. The present disclosure is not necessarily limited to the particular embodiments described and illustrated herein.

DETAILED DESCRIPTION

Referring to FIGS. 1 and 4-7, a fitness training device 100 may include an elongated deck 104 supported by one or more wheel bracket structures 106 (e.g., one or more wheel brackets 108). The deck 104 may include a top surface 112, a bottom surface 116, opposing first and second side edges 120, 124 and opposing front and rear longitudinal edges 128, 132. The side edges 120, 124 and the longitudinal edges 128, 132 collectively form a periphery or perimeter of the deck 104. The deck 104 may be quadrilaterally shaped and may include a longitudinal length L extending between the opposing first and second side edges 120, 124 and a transverse width W extending between the opposing front and rear longitudinal edges 128, 132. In some embodiments, the length L may be greater than the width W such that the top surface 112 of the deck 104 is substantially rectangular. Decks of other shapes may be suitable, including those where the side edges 120, 124 and/or the front and rear longitudinal edges 128, 132 are at least partially non-linear. In one embodiment, the deck 104 may include a thickness T that is substantially less than its length L or width W such that the deck 104 is considered to have a thin profile (see FIG. 6). As explained in more detail below, the thin profile of the deck 104 may provide, in combination with the wheel bracket structure 106 (such as wheel brackets 108), a desired aesthetic or functional characteristic (e.g., a low deck height) of the fitness training device 100.

Figure 4:
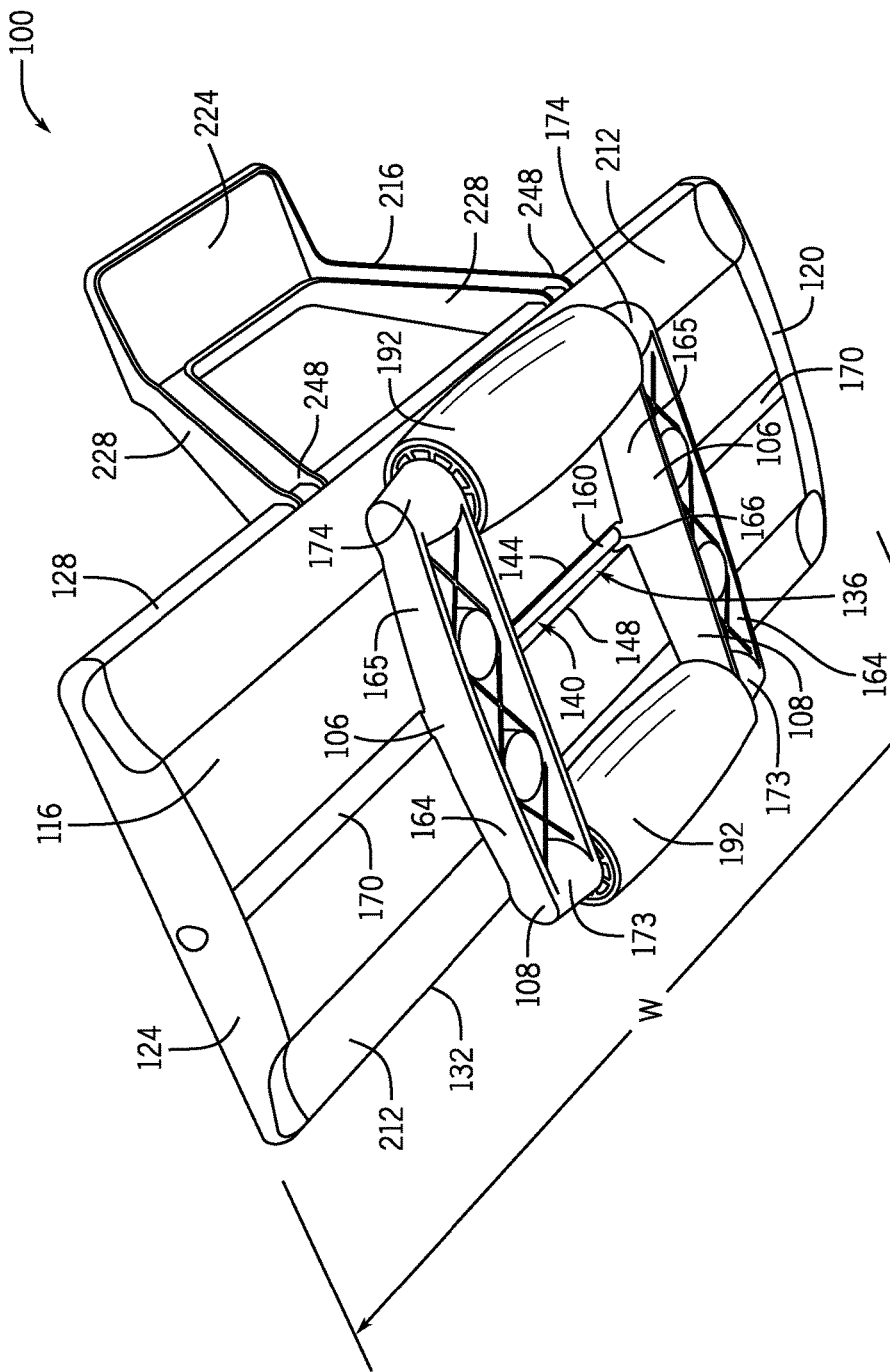
FIG. 4 is a perspective view of the fitness training device shown from the underside.
Figure 5:
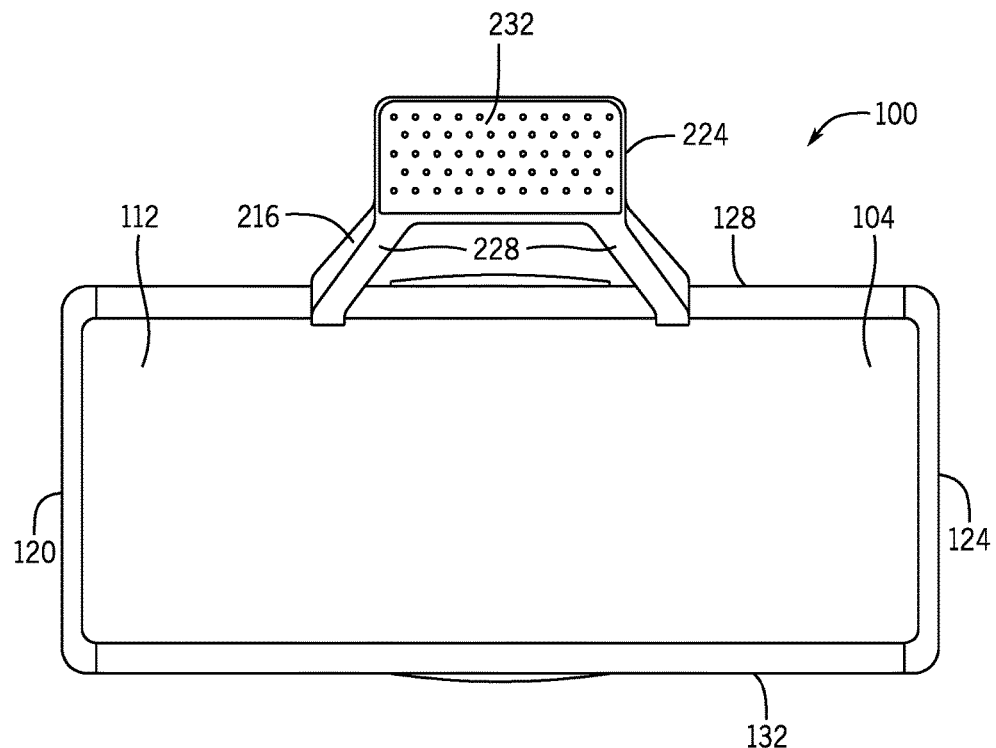
FIG. 5 is a top view of the fitness training device.
Figure 6:
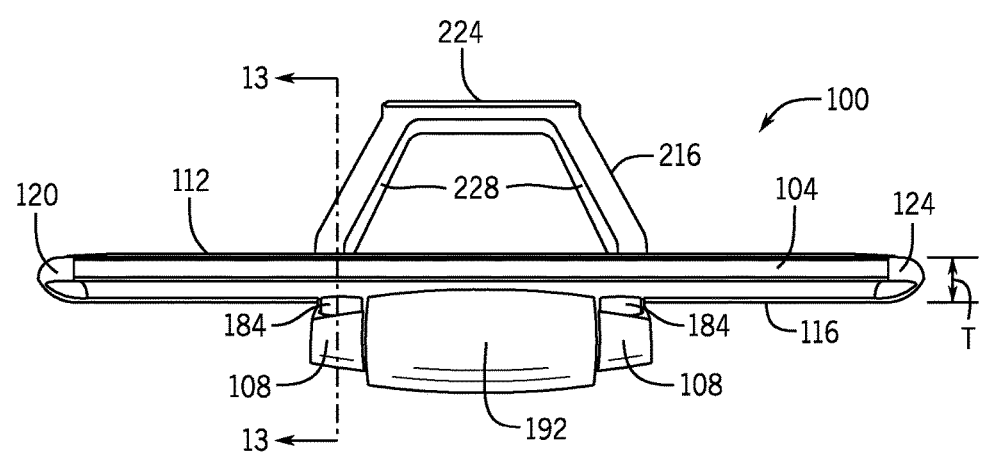
FIG. 6 is a front view of the fitness training device.
Figure 11:
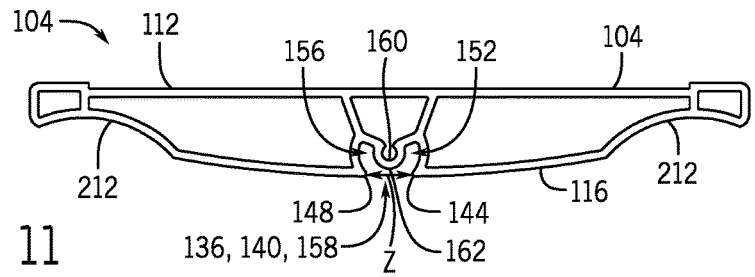
FIG. 11 is a side elevation view of a deck of the fitness training device.

With reference to FIGS. 4 and 11, a slot or channel 136 may be defined in the bottom surface 116 of the deck 104 to receive at least a portion of the wheel brackets 108 and allow relative movement there between, as more fully explained below. The slot 136 extends at least partially or entirely along the distance between the opposing first and second side edges 120, 124, and in one example the slot 136 extends along the center of the deck 104 (i.e., centered between the front and rear longitudinal edges 128, 132 of the deck 104). The slot 136 may not be continuous along its extension, and may instead be segmented. The slot 136 may be C-shaped in cross-section. In such embodiments, the C-shaped slot 136 may define a recess including a central portion or gap 158 defined between first and second edges 144, 148 and having a width dimension Z; and first and second curved troughs 152, 156 extending respectively away from the bottom surface 116 to define a central rib 160. As best seen in FIG. 11, the rib 160 defines a rounded lower surface 162 having a convex shape to define at least a portion of the C-shaped slot 136. The rib 160 in at least one example may not extend to or below the first and second edges 144, 148, and may be formed along the entire length or only along a part of the entire length of the channel 136. The channel 136 may operably engage with a feature of the wheel brackets 108, described below, and permit the wheel brackets 108 to move, rock, or pivot relative to the deck 104 along a pivot line P during balancing movement. In some embodiments, the pivot line P may be created by a centerless hinge structure so as to provide a virtual pivot axis spaced away from the engagement between the deck 104 and the wheel brackets 108.

With reference to FIGS. 4, 7, 9, and 10, the wheel bracket structure 106 is positioned below the deck 104 and rotatably supports at least two wheels as noted below. The wheel bracket structure 106 is configured to engage the deck 104, such as at the bottom surface 116, to allow relative movement between the deck 104 and the wheel bracket structure 106. The relative movement between the deck 104 and the wheel bracket structure 106 may be a tilting movement about a pivot line P defined by the engagement between the two. In one example, the wheel bracket structure 106 may include at least two wheel brackets 108. Each wheel bracket 108 may be an elongated member having opposing arms 164 and 165, each defining an end 173, 174 respectively. Each wheel bracket 108 may be coupled to the bottom surface 116 of the deck 104 near an end thereof, such as adjacent one of the opposing side edges 120, 124. In some embodiments, each wheel bracket 108 extends perpendicular to the length L of the deck 104 and between the opposing front and rear longitudinal edges 128, 132 of the deck 104.

Figure 9:
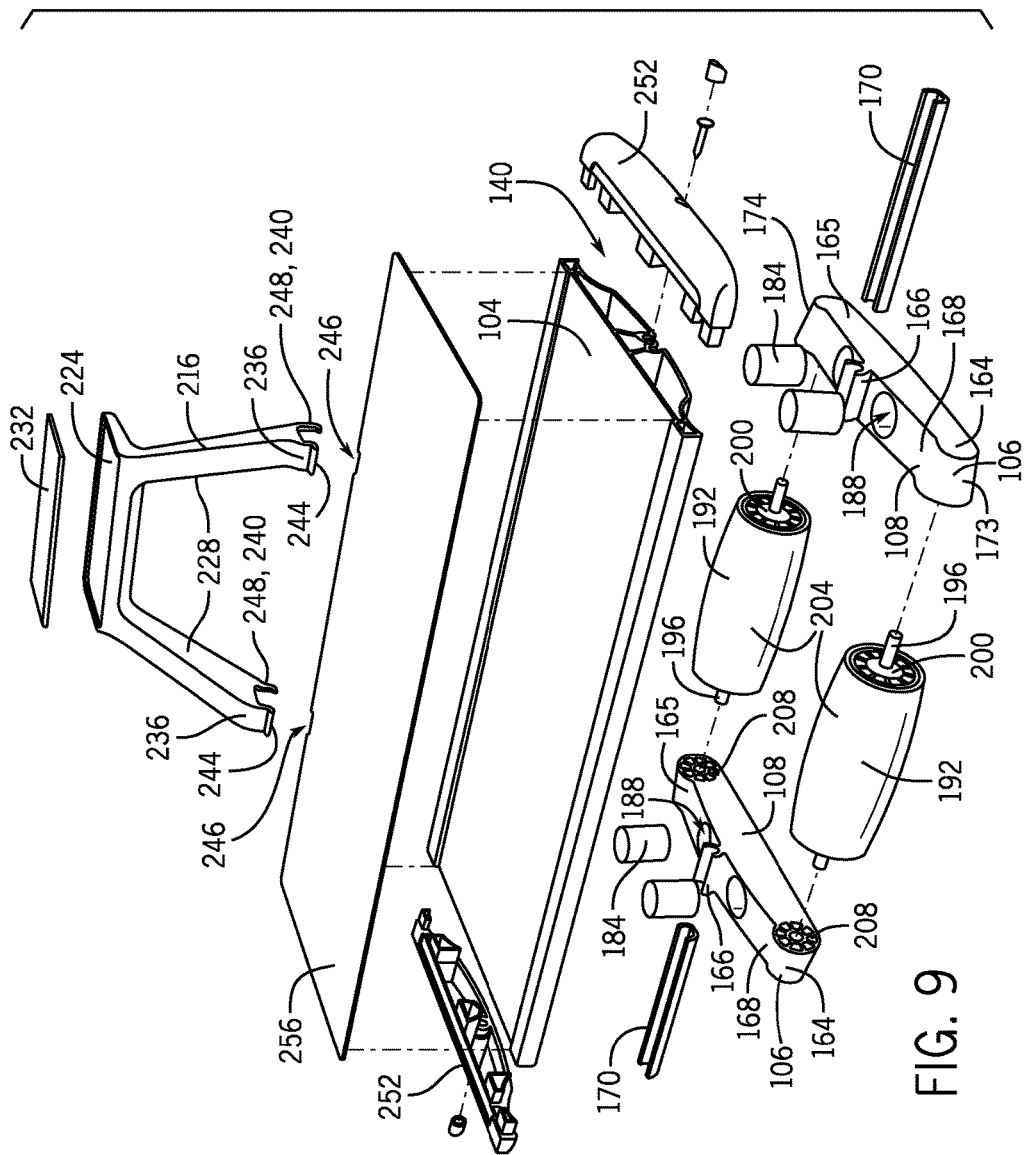
FIG. 9 is an exploded perspective view of the fitness training device.
Figure 10:
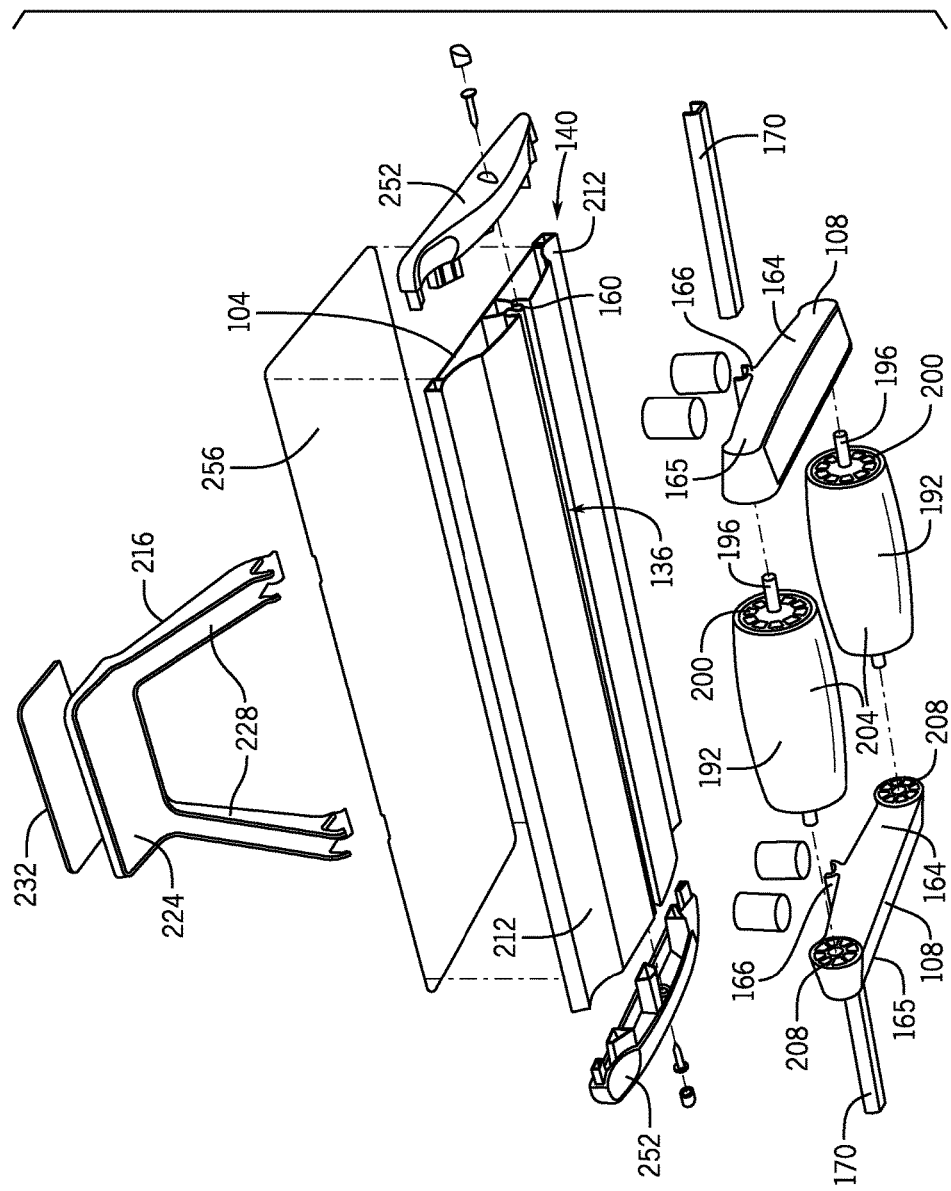
FIG. 10 is another exploded perspective view of the fitness training device.
Figure 12:
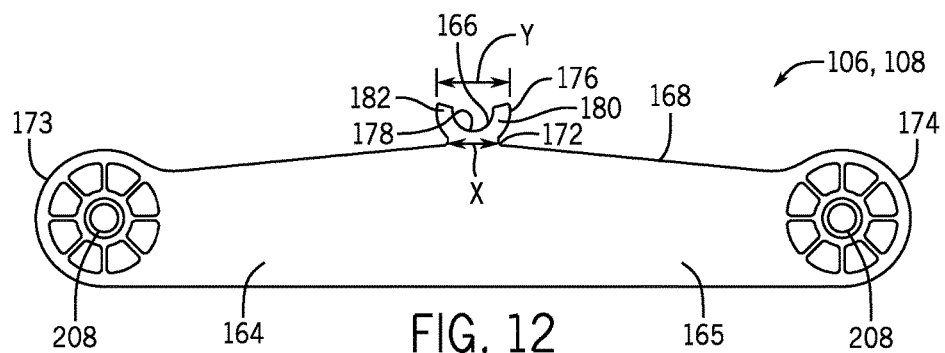
FIG. 12 is side elevation view of a wheel bracket of the fitness training device.

Turning to FIGS. 9, 10, and 12, each wheel bracket 108 may include a securement structure 166 defined on an upper surface 168 of each wheel bracket 108. In such embodiments, the securement structure 166 may be received at least partially within the slot 136 to form a joint, or connection structure, 140, and may translate or slide along the length of the slot 136 to position the wheel bracket 108 along the length L of the deck 104 between the opposing first and second side edges 120, 124 (see FIG. 4). To attach each wheel bracket 108 to the deck 104, the securement structure 166 is aligned with and inserted into the slot 136, and slides along the slot 136 to a desired position. The wheel bracket structure 106 may include a single structure where the separate wheel brackets 108 are joined together, either integrally as one piece or by connection brackets or the like. The securement structure 166 may extend along the upper surface 168 thereof and be received in the slot 136 similarly to that described above. Additionally, the wheel bracket structure 106 may also be integrally formed and/or secured to the deck 104 to form a single unit, with the engagement between the deck 104 and wheel bracket structure 106 being formed by a living hinge type structure or other flexible structure not requiring two or more separate elements joined together.

In some embodiments, the securement structure 166 may be secured within the slot 136 to limit unintentional disengagement of each wheel bracket 108 from the deck 104. When the securement structure 166 is received in the slot 136, the engagement between the slot 136 and the securement structure 166 forms the joint or connection structure 140 that retains the securement structure 166 within the slot 136. The connection structure 140 allows the securement structure 166 and the deck 104 to pivot or rotate relative to each other about the pivot line P formed generally along the engagement region between the rib 160 and the securement structure 166. This relative movement allows variation in the angle θ (see FIG. 13) to accommodate relative movement between the deck 104 and each wheel bracket 108. In such embodiments, the motion may be a rocking motion from front to back about the rib 160, as detailed below (see FIG. 17). In embodiments having a plurality of wheel brackets 108, the engagement of each wheel bracket 108 within a corresponding segment of the channel 136 creates a pivot line P for each wheel bracket 108. In some embodiments, each pivot line P may be aligned with each other to create a common pivot line P. The pivot line P may extend the entire distance or only partially along the distance between the side edges 120, 124. To secure the wheel brackets 108 in position relative to the opposing first and second side edges 120, 124, a pair of bracket spacers 170 may be positioned at least partially in the slot 136 between the wheel brackets 108 and the respective first and second side edges 120, 124 of the deck 104. The bracket spacers 170 may abut the securement structure 166 of the wheel brackets 108.

Figure 13:
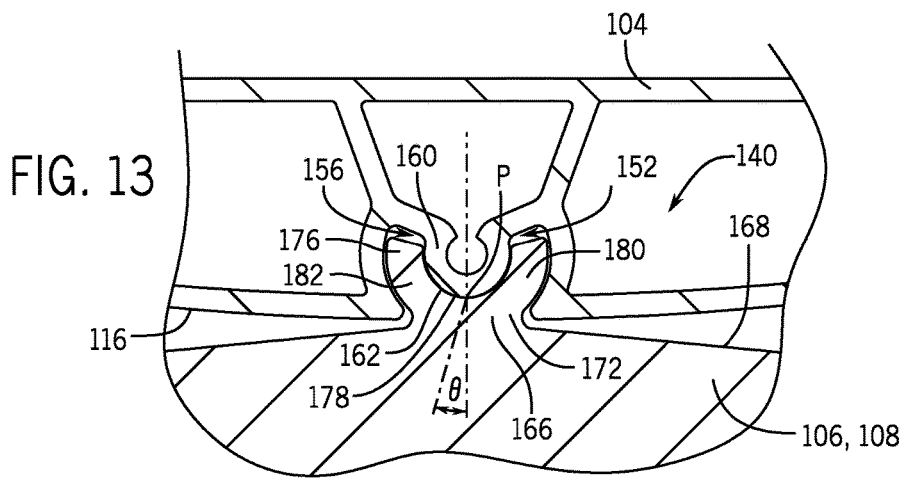
FIG. 13 is a fragmentary cross-sectional view the engagement between the deck and the wheel bracket taken along line 13-13 of FIG. 6.

Turning to FIGS. 12 and 13, the securement structure 166 extends upwardly from the upper surface 168 of the wheel bracket 108, and may include a first portion 172 and a second portion 176. The first portion 172 is a neck or base defining a width dimension X, and supports the second portion 176. The second portion 176 defines an upward "U" shape having a concave upper surface 178 and opposing curved arms 180 and 182 extending away from one another and defining a width dimension or span Y. When the securement structure 166 is engaged with the slot 136, the second portion 176 is received in and retained within the slot 136, with arms 180 and 182 received in the first and second troughs 152 and 156, respectively, and the first portion 172 positioned in the gap 158. The arms 180, 182 may extend around a small arc-portion of the convex lower surface 162 of the rib 160, or may extend around up to and greater than a 180 degree arc portion of the rib 160, as best seen in FIG.

13. The arms 180, 182 and the corresponding troughs 152, 156 may have similar curvature for a precise but relatively movable fit. The features of the securement structure 166 are generally smaller in dimension than the features of the slot 136 to allow a relatively loose fitting. For instance, the arms 180, 182 are shorter and thinner than the troughs 152, 156 in which they are received, and the width dimension X of the first portion 172 is smaller in dimension than the width dimension Z of the gap 158 of the slot 136; resulting in gaps or spaces between the walls forming the slot 136 and the securement structure 166 where the structures are not in engagement (See FIG. 12).

The securement structure 166 is retained in the slot 136 because the span or width dimension Y of the arms 180, 182 is greater than the width dimension Z of the gap 158 of the slot 136. In this example, the securement structure 166 may be loosely received within the slot 136, with the concave upper surface 178 of the securement structure 166 engaging the convex lower surface 162 of the rib 160, defining the pivot line P, about which the deck 104 pivots or rotates relative to each wheel bracket 108 to tilt and provide a desired element of instability for balance improvement.

Referring to FIGS. 4 and 6-10, the fitness training device 100 may include a plurality of wheels 192 or rollers (e.g., at least two wheels 192) rotatably supported by the wheel bracket structure 106, such as in this embodiment two wheel brackets 108, to provide lateral instability and permit the fitness training device 100 to traverse across a support surface (e.g., the ground). In some embodiments, the wheel design may be elongated with a relatively small diameter (e.g. low and wide, shaped like a roller), where the diameter changes along the length of the wheel 192 to define a convex curved shape (e.g., barrel-shape) on its outer surface or peripheral portion. In this example, the diameter of the wheels 192 at opposing ends are smaller than the diameter of the wheel 192 at or near its mid-point; and the mid-point of each wheel 192 may be in contact with the ground or support surface when the deck 104 is substantially parallel to the ground or support surface.

Figure 18:
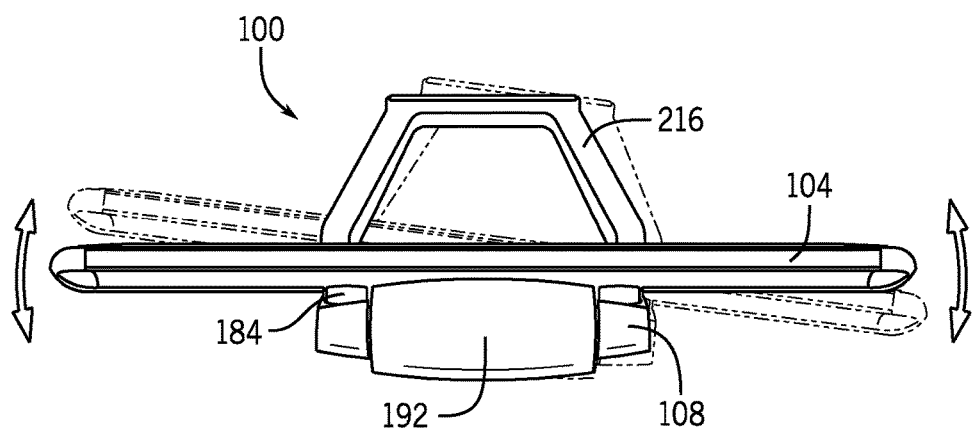
FIG. 18 is a front view of the fitness training device.
Figure 30:
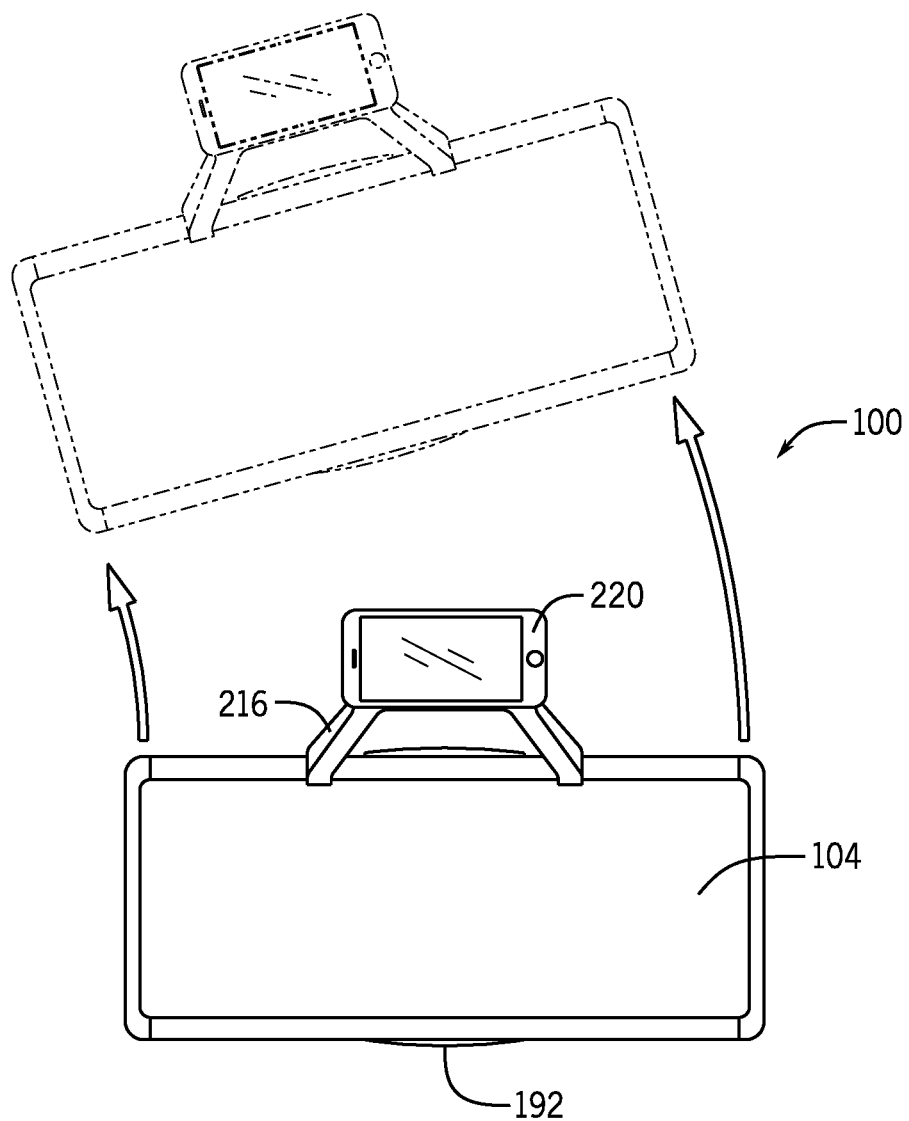
FIG. 30 is a top view of the fitness training device performing arcing turns.
Figure 31:
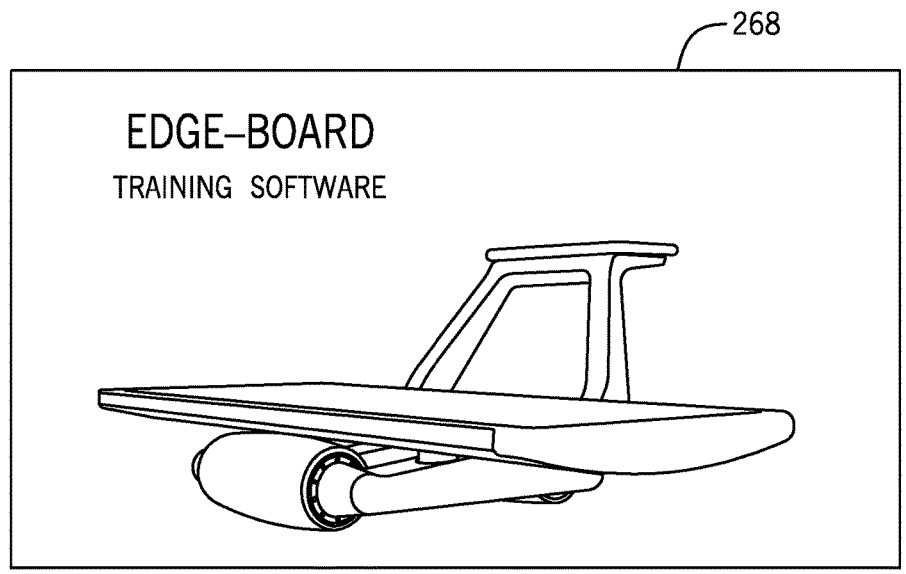
FIGS. 31-38 illustrate an embodiment of a fitness training software associated with the fitness training device.
Figure 32:
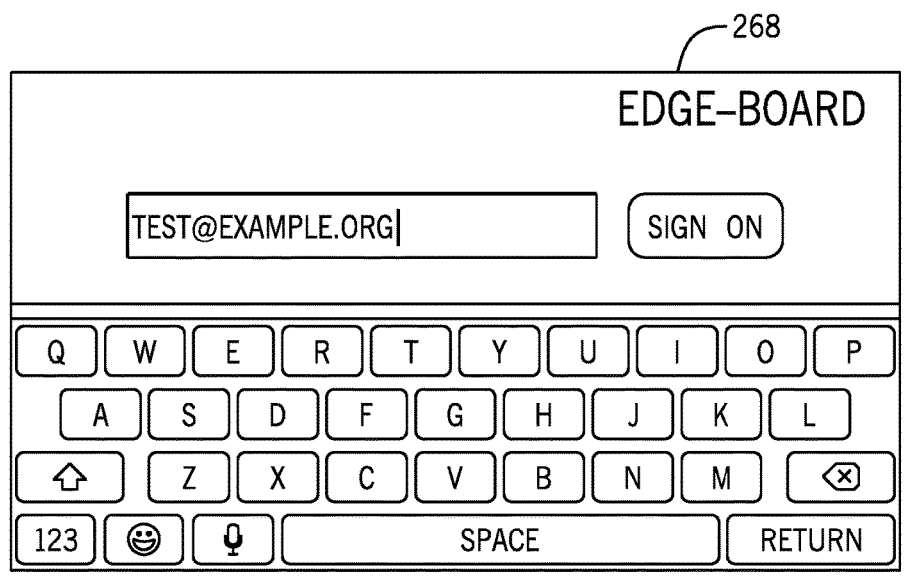

The convex shape of the wheel 192 may allow the deck 104 to rock slightly along the length L of the deck 104 between the opposing first and second side edges 120, 124 of the deck 104, thereby providing a degree of lateral instability (see FIG. 18). In some embodiments, the convex wheel shape may allow the fitness training device 100 to be steered into broad arcing turns (see FIG. 30), enabling a broader range of movements and engaging a broader range of muscle groups. The diameter, width, and curvature, among others, of each wheel 192 affect the stability or instability of the fitness-training device 100. For example, the wider the wheel 192, the more stable the fitness training device 100 during use. Conversely, the more convexly-shaped the wheel 192, the less stable the fitness training device 100 during use. Though shown and described as having a barrel-shape, in some embodiments, the wheel 192 may have a right-cylindrical shape. In one or more examples of embodiments, the wheel 192 may be about 2.1" in maximum diameter and about 4.7" wide. Each wheel 192 may be positioned to rotate about an axis parallel to the pivot line P.

Referring to FIGS. 9 and 10, each wheel 192 may include a wheel axle 196, a wheel core 200 rotatably supported by the wheel axle 196, and a wheel tread 204 substantially surrounding the wheel core 200. In some embodiments, the wheel core 200 may be permanently connected to the wheel axle 196 (e.g., press-fit) and may be constructed of a hard injection-molded plastic, metal, or other suitable material. Similarly, the wheel tread 204, which may be substantially smooth or include a tread pattern, may be permanently molded over the wheel core 200 and may be constructed from cast rubber, urethane, or injection molded thermoplastic elastomer (TPE). In some embodiments, the convex shape of the wheels 192 may be provided by the wheel core 200, the wheel tread 204, or a combination of both. Each wheel bracket 108 may include support structures 208 to secure the wheels 192 to the wheel brackets 108. In some embodiments, the support structures 208 may include a set of ball bearings or other bearing structure or assembly, which in turn rotatably support the wheel axle 196. In some embodiments, the wheel axle 196 may be press-fit into the support structures 208 to limit rotation of the wheel axle 196 relative to the wheel brackets 108. In such embodiments, the wheel core 200 may include one or more bearings to permit rotation of the wheels 192.

Figure 7:
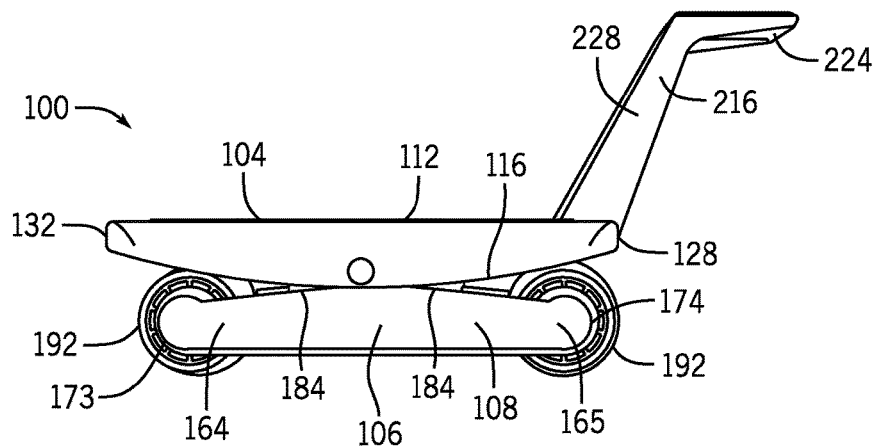
FIG. 7 is a side view of the fitness training device.
Figure 8:
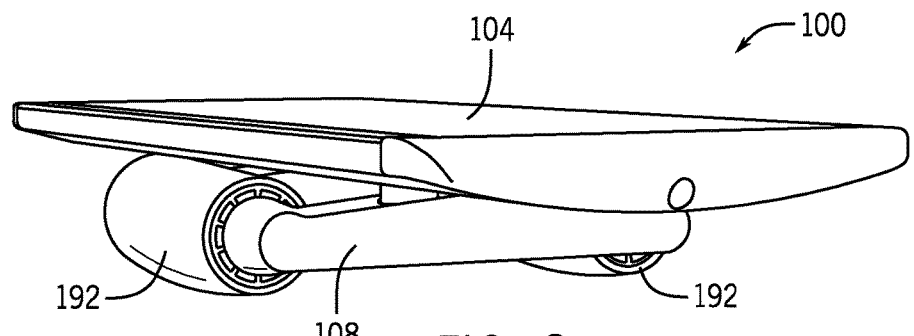
FIG. 8 is a perspective view of the fitness training device without the phone bracket attachment.
Figure 17:
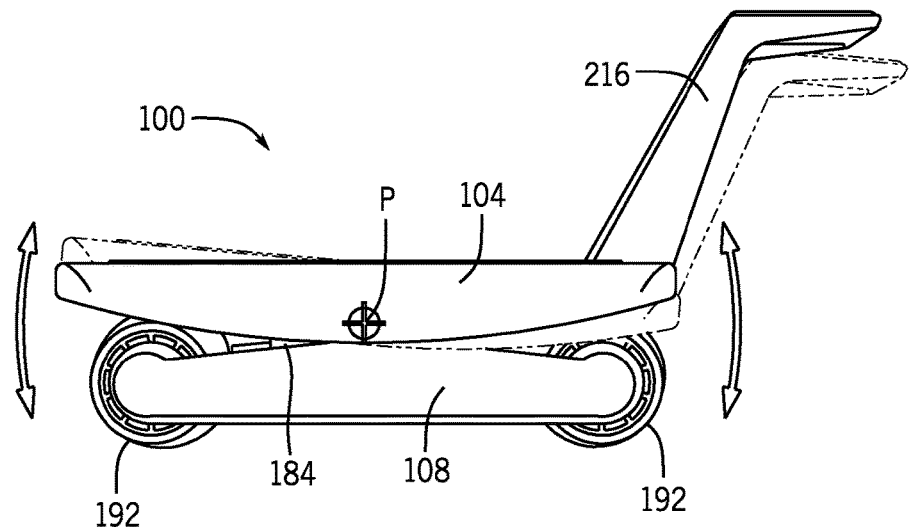
FIG. 17 is a side view of the fitness training device.

Turning to FIGS. 7 and 17, the wheels 192 may be tucked or positioned under the deck 104 such that a majority (e.g., greater than 50%, greater than 60%, greater than 70%, greater than 80%, greater than 90%, or 100%) of a diameter of each wheel 192 is positioned vertically below the deck 104. In some examples, the diameter of each wheel 192 does not extend beyond a vertical plane defined by the perimeter of the deck 104. The wheels 192 may be positioned symmetrically or asymmetrically across the pivot line P, or may be equally or unequally spaced from the front and rear longitudinal edges 128, 132 of the deck 104. Positioning the wheels 192 under the deck 104 provides various advantages. For example, it allows the overall product to be compact and portable, thus making it easier for the user to fit the fitness training device 100 conveniently into a gym bag or back pack, for instance. Additionally, positioning adjacent wheels 192 close together makes it easier to perform arcing turns while the deck 104 is rolling (see FIG. 30). Alternatively, positioning adjacent wheels 192 further apart provides greater stability to the fitness training device 100.

Figure 41:
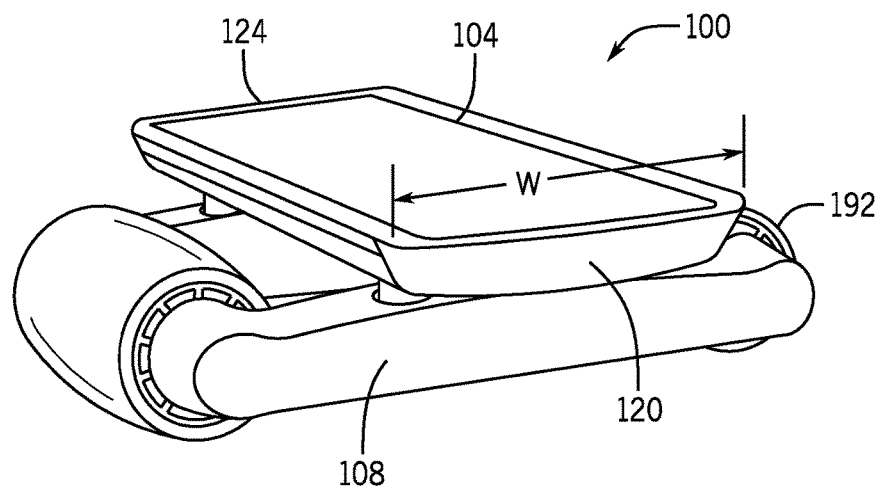
FIG. 41 is a perspective view of an additional embodiment of the fitness training device, with the wheels positioned substantially outboard the deck.

Alternatively, in some embodiments, the deck 104 and/or the wheel brackets 108 may be sized and shaped to position a majority of the wheels 192 substantially beyond the vertical plane defined by the perimeter of the deck 104 (see FIG. 41). In the embodiment of FIG. 41, a minority (e.g., less than 20%, less than 10%, or 0%) of the diameter of each wheel 192 is positioned vertically below the deck 104. Positioning the wheels 192 substantially outboard of the deck 104 provides various advantages; including providing increased stability for use on uneven surfaces. In the embodiment of FIG. 41, a user may place a single foot on the deck 104 lengthwise between the opposing first and second side edges 120, 124. In some embodiments, the width W of the deck 104 may at least match, or approximately match the width of a user's foot or may be greater. For example, the width W may be in the range of approximately 4 to 8 inches, and the length of the deck 104 (between the side edges 124 and 120) may be in the range of approximately 8 to 15 inches. In such embodiments, the fitness training device 100 may be used to improve single foot balance control. In some embodiments, a user may use the fitness training device 100 of FIG. 41 with each foot to improve functional balance control for various sport or fitness applications (e.g., skating, skiing, etc.)

With reference to FIGS. 4, 10, and 11, the bottom surface 116 of the deck 104 may be sized and shaped to provide a low deck height. For instance, the bottom surface 116 may include one or more recess portions 212 formed proximate to the front and rear longitudinal edges 128, 132 of the deck 104 and sized for at least partial receipt of the peripheral portions of the wheels 192 therein. The recess portions 212 may each have a smooth surface with a downwardly concave-shape. The shape of each recess portion 212 may generally match the curvature of the corresponding wheel 192, or may have a different shape to enhance a braking effect, as described below. The recess portions 212 may have a roughened surface (in part or entirety) or may be ribbed along or across the length direction of the wheel 192, to enhance the braking effect. In such embodiments, the top surface 112 of the deck 104 may be positioned close to the support surface while enabling a larger diameter wheel 192. The benefit of a low deck height may include having feet of a user closer to the ground to provide a more natural movement for exercises such as lunges. In one or more examples of embodiments, the deck height may be about 2.0" to about 3.0" off the ground (e.g., 2.85" off the ground). A lower deck height may compromise the ability of the deck 104 to rock or pivot, and may limit the diameter of the wheels 192. If the wheel diameter is too small, the wheel 192 may not roll well on certain support surfaces (e.g., plush carpet or grass).

In some embodiments, when the deck 104 is tilted during use, a portion of the deck 104 moves towards an adjacent wheel 192, and a different portion of the deck 104 moves away from an adjacent wheel 192 (see FIG. 17). The movement of the deck 104 towards an adjacent wheel 192 is resisted or dampened by one or more resilient damping members 184 (e.g., compressible rubber pads, compression springs, torsion springs, or leaf springs, among others) situated at least partially between the deck 104 and the opposing arms 164, 165 of each wheel bracket 108. The damping members 184 may be rubber bumpers having a right-cylindrical shape, and may be received at least partially within blind hole cavities 188 defined in the upper surface 168 of each wheel bracket 108 to secure their position during use, and may also contact the bottom surface 116 of the deck 104 during balance movement of the fitness training device 100 (see FIG. 7). The engagement of the resilient damping member(s) 184 and the bottom surface 116 of the deck 104 may be unconstrained to allow the top of the resilient damping member(s) 184 to adjust to the different loads applied by the deck 104 during use. In such embodiments, the damping members 184 may resiliently resist pivoting movement of the wheel brackets 108 relative to the deck 104 about the pivot line P. In some embodiments, the damping members 184 may be operable to maintain the top surface 112 of the deck 104 substantially parallel to the floor absent external forces on the deck 104 (see FIGS. 6 and 7). In some embodiments, the damping members 184 may be harder, softer, or a combination, on each side as desired by the user or for enhancing particular balance exercises.

Referring now to FIGS. 1-7, 9, and 10, the fitness training device 100 may include a bracket 216 to hold or otherwise secure a sensing device 220 (e.g., a smartphone, tablet, or other sensing mechanism). The bracket 216 may include a support member 224 and a pair of bracket pillars 228 extending from the support member 224. The support member 224 may be substantially planar and, in some embodiments, may extend generally parallel to the top surface 112 of the deck 104. The bracket pillars 228 may be elongate members extending from the support member 224 to the deck 104 (e.g., to the top surface 112) such that the support member 224 is positioned forward of the first longitudinal edge 128 so as to not interfere with placement of a user's hands and/or feet during balancing movement. In some embodiments, the bracket 216 may include means to hold the sensing device 220. For example, a mounting pad 232, which may be formed from silicone rubber and may be sticky or include a gripping feature, may be situated on top of the support member 224 to hold the sensing device 220 (see FIG. 3). Silicone rubber may be inexpensive, easy to use, and has a track record of reliability; however, other mechanical methods of attachment could be used for securing the sensing device 220 including straps, tabs, and magnets. In various embodiments, the fitness training device 100 may be integrally formed with an integrated sensing device. While a phone may be used for purposes of reference, any suitable device having the proper components and software may be used. For example, a device having a microprocessor, memory, network communication, gyroscope/accelerometer or other suitable sensing means may be used.

In some embodiments, the bracket 216 may be designed to be removable, thus allowing the overall system to be more compact and portable for transporting in a gym bag, for instance. A removable bracket 216 may also allow for use of the fitness training device 100 without the bracket 216 (see FIG. 8). The removable bracket 216 may be positioned on the deck 104 such that the two bracket pillars 228 do not interfere with the user placing a foot on the deck 104 length-wise or sideways, or when both feet or both hands are placed on the ends of the deck 104. In some embodiments, each bracket pillar 228 may include first and second attachment portions 236, 240 to removably secure the bracket 216 to the deck 104. In such embodiments, the first attachment portion 236 may include a tab 244 designed to be received within a corresponding slot or opening 246 defined in the top surface 112 of the deck 104 (see FIG. 9). The second attachment portion 240 may include one or more hook-like members 248 that abut or engage a portion of the deck 104 (e.g., the front longitudinal edge 128 of the deck 104) to define an attached position of the removable bracket 216 (see FIG. 4). In some embodiments, the members 248 may clip over the front longitudinal edge 128 of the deck such that the members 248 contact both the top and bottom surfaces 112, 116 of the deck.

Figure 2:
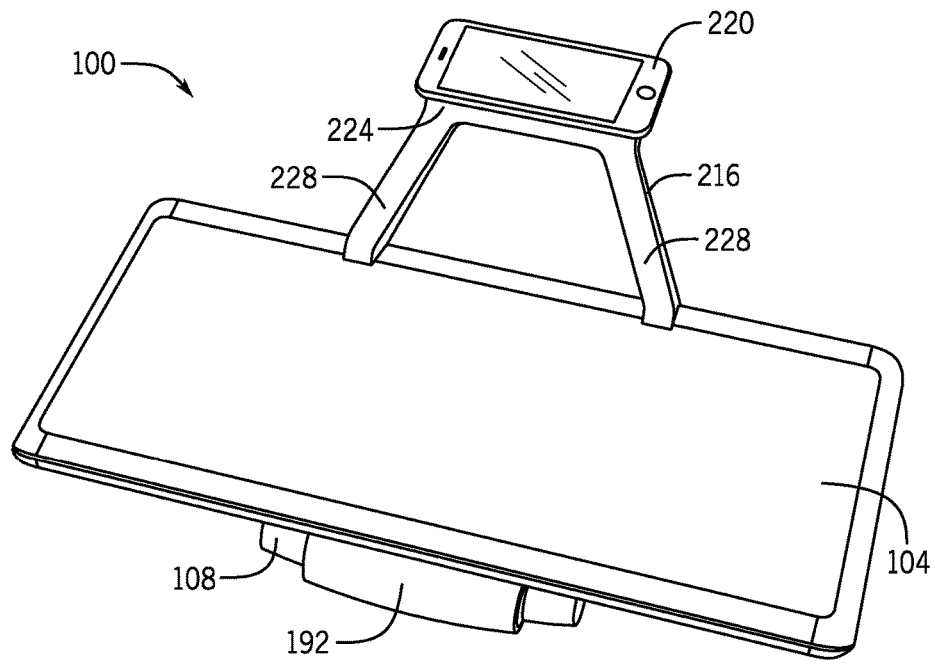
FIG. 2 is a perspective view of the fitness training device of FIG. 1, with a smartphone placed on a phone bracket.
Figure 3:
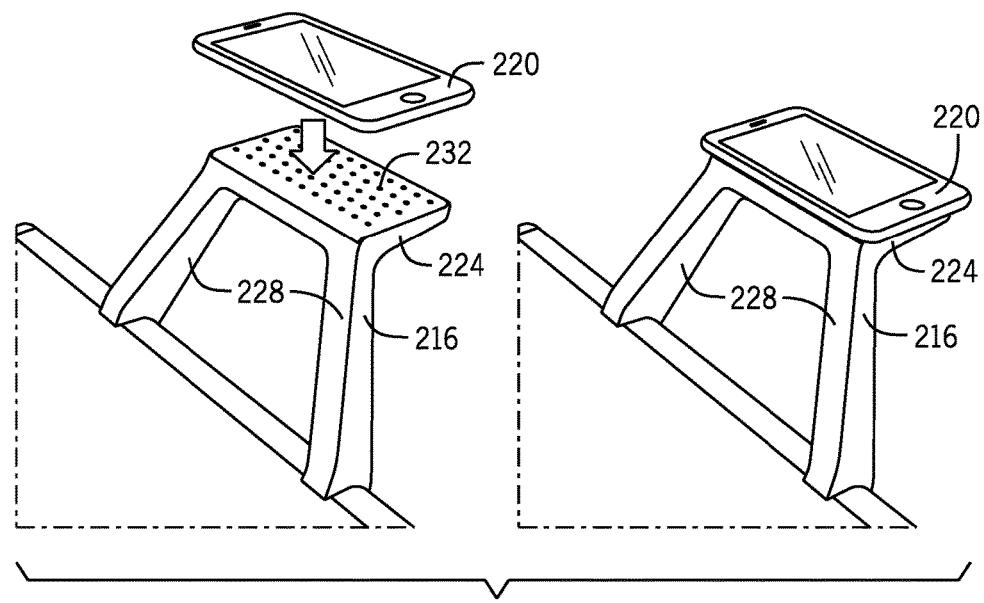
FIG. 3 is two close-up perspective views of the phone bracket, one with the smartphone hovering over the bracket, and one with the smartphone positioned on the bracket.
Figure 15:
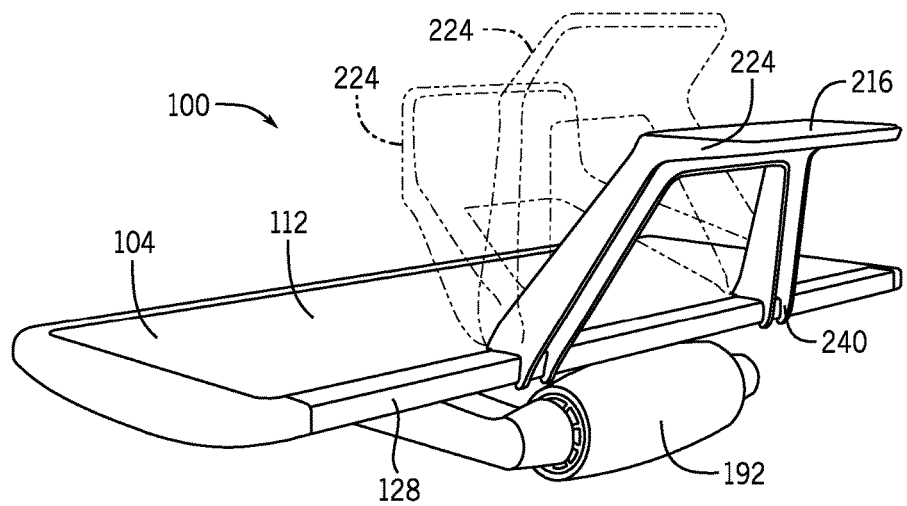
FIG. 15 is a perspective view of the fitness training device.
Figure 16:
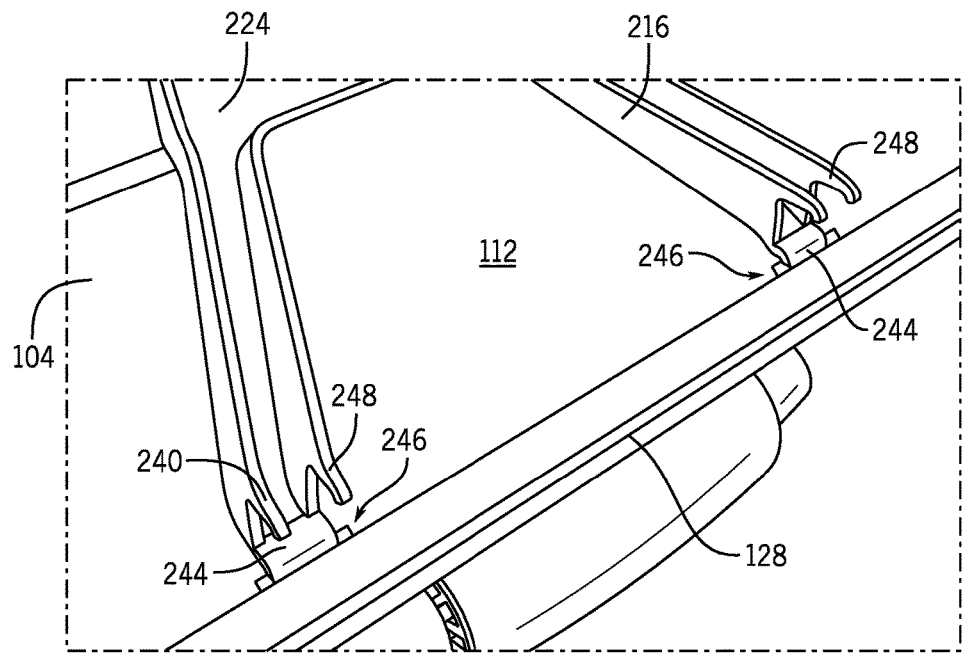
FIG. 16 is an enlarged fragmentary view of the fitness training device.
Figure 19:
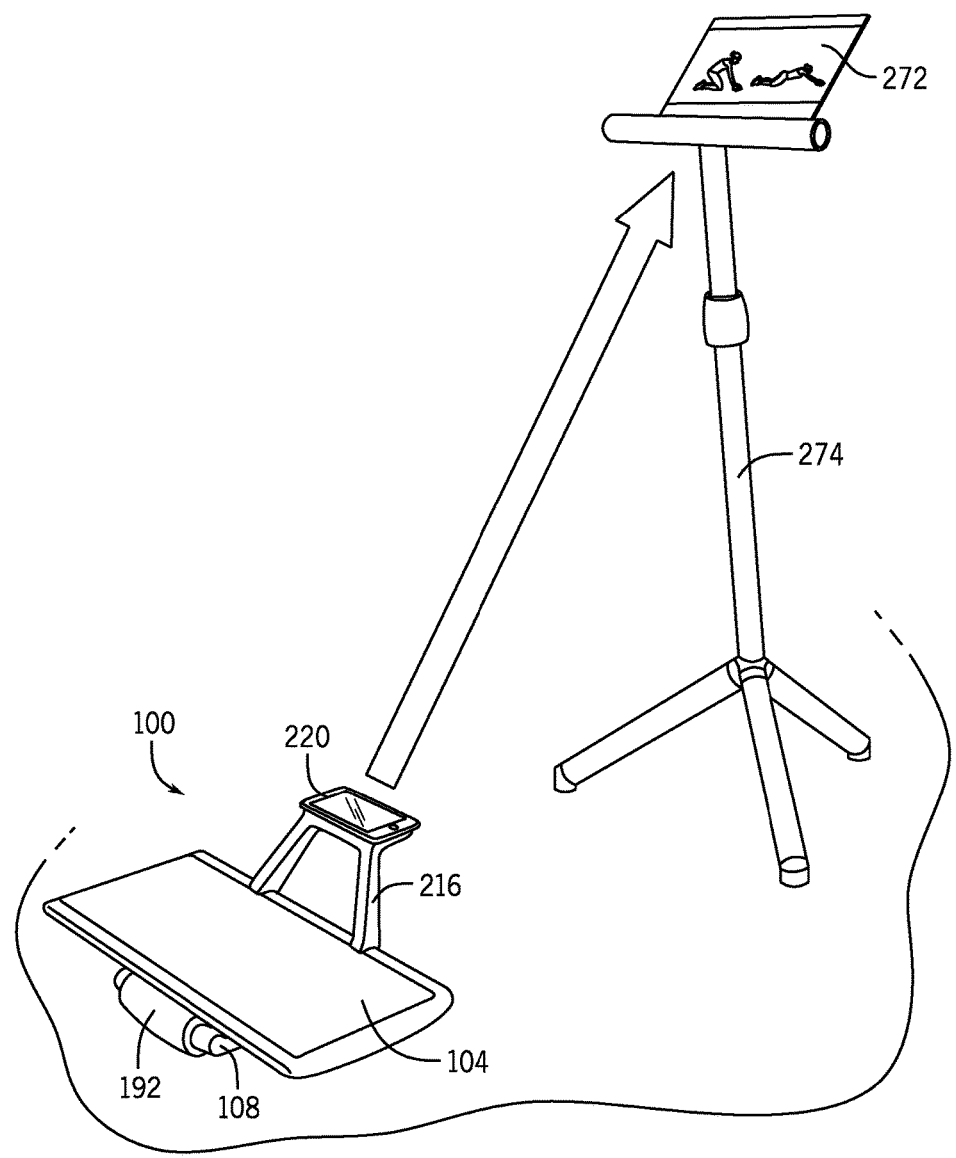
FIG. 19 is a perspective view of the fitness training device and a tablet display supported by a stand.
Figure 20:
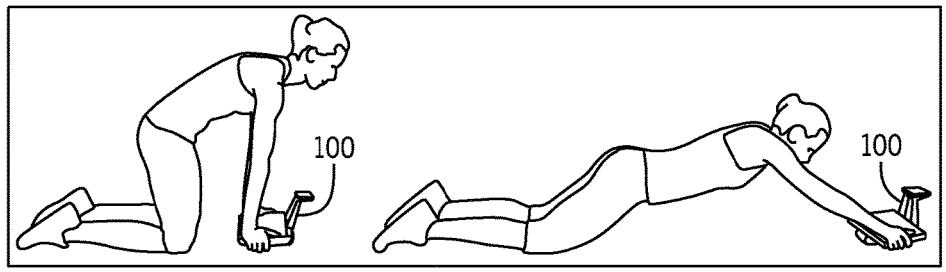
FIG. 20 shows a user using the fitness training device to perform an abdominal extension exercise.
Figure 21:
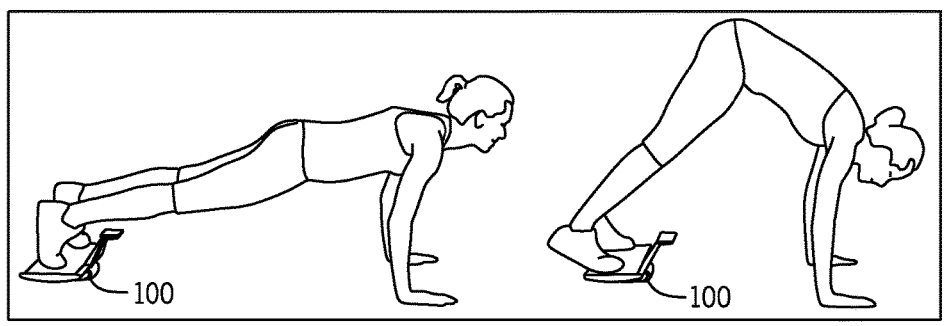
FIG. 21 shows a user using the fitness training device to perform a pike up exercise.
Figure 22:
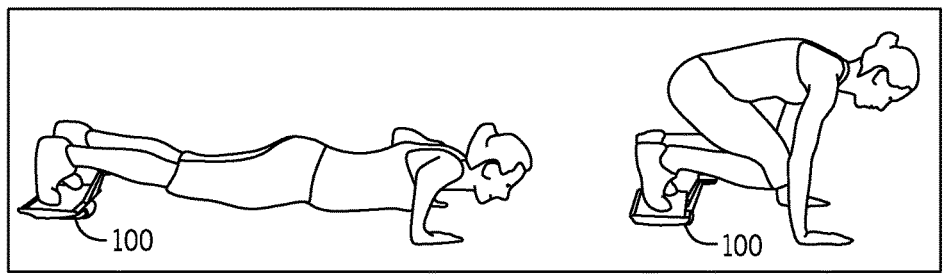
FIG. 22 shows a user using the fitness training device to perform an atomic pushup exercise.
Figure 23:
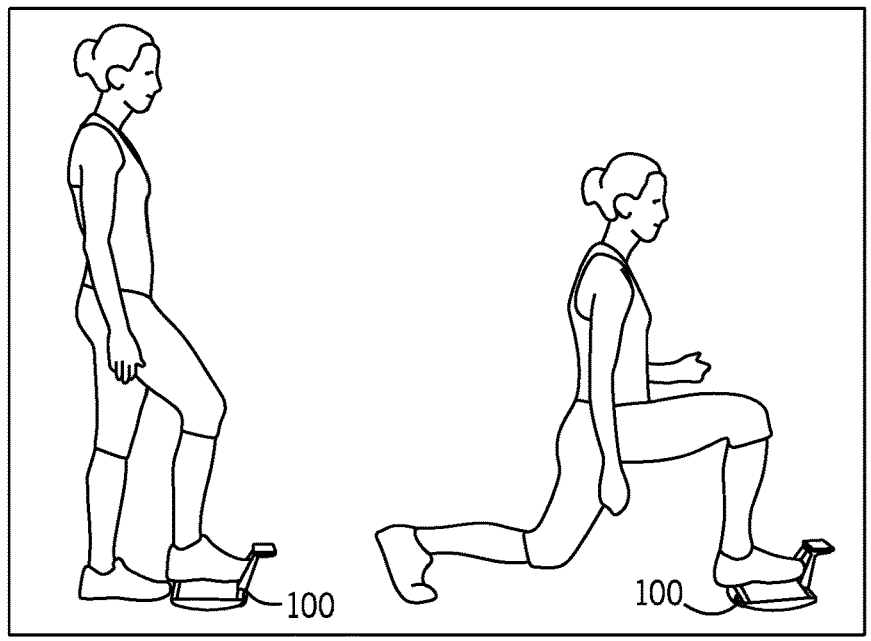
FIG. 23 shows a user using the fitness training device to perform a front lunge exercise.

Turning to FIGS. 15 and 16, to attach the bracket 216 to the deck 104, the bracket 216 may be first positioned such that the support member 224 extends at an angle (e.g., about 7 degrees) relative to the top surface 112 of the deck 104 so the tab 244 of each first attachment portion 236 can be inserted within the respective opening 246 defined in the deck 104. The bracket 216 may be subsequently rotated away from the top surface 112 of the deck 104 until the support member 224 is generally parallel to the top surface 112 as defined by the second attachment portion 240 contacting the front longitudinal edge 128 of the deck 104. The bracket 216 may be removed by reversing the steps above. The example shown in FIGS. 15 and 16 is non-limiting, representing one or more possible embodiments. Alternative methods may include hinged, flip-up design similar to a laptop screen, or mounting the sensing device 220 directly onto the deck 104 of the fitness training device 100. FIGS. 2, 3, and 19 show a smartphone mounted to the bracket 216; however, alternative methods of tracking movement could include using a smart watch, activity tracker, iPod Touch, or other device containing sensors. The sensors could also be custom designed and either permanently placed inside the fitness training device 100 or as a removable module.

Figure 14:
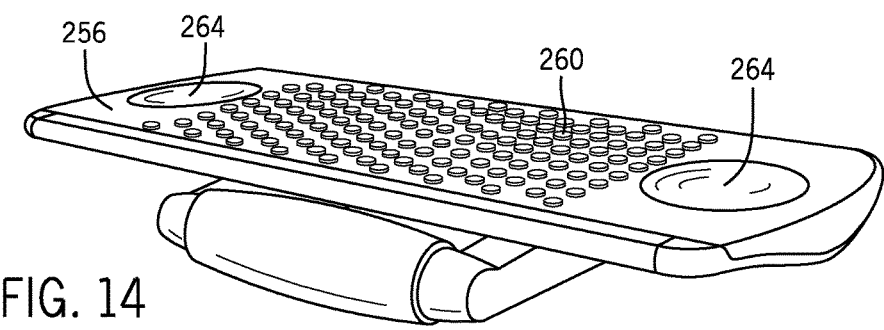
FIG. 14 is a perspective view of the fitness training device.

Referring to FIGS. 9 and 10, the fitness training device 100 may include other convenience and/or safety features. For instance, in some embodiments, the fitness training device 100 may include a pair of end caps 252 connected to the opposing first and second side edges 120, 124 of the deck 104. For example, the deck 104 may have two plastic injection-molded end caps 252 to enclose the opposing first and second side edges 120, 124 and secure the bracket spacers 170 and/or wheel brackets 108 within the slot 136. A pad or other gripping surface may be provided on the top surface 112 of the deck 104, such as a rubber deck pad 256 which may be adhered to the deck 104 with glue or pressure-sensitive adhesive (PSA). The deck pad 256 may be textured and may include a plurality of gripping features 260 to limit slipping of a user's hands and/or feet when placed on the fitness training device 100 (see FIG. 14). In some embodiments, the deck pad 256 may extend over each of the opposing first and second side edges 120, 124 of the deck 104 and onto the end caps 252. The end caps 252 may be soft and waterfall-shaped to improve user comfort when the end caps 252 are held in a user's hands.

Figure 42:
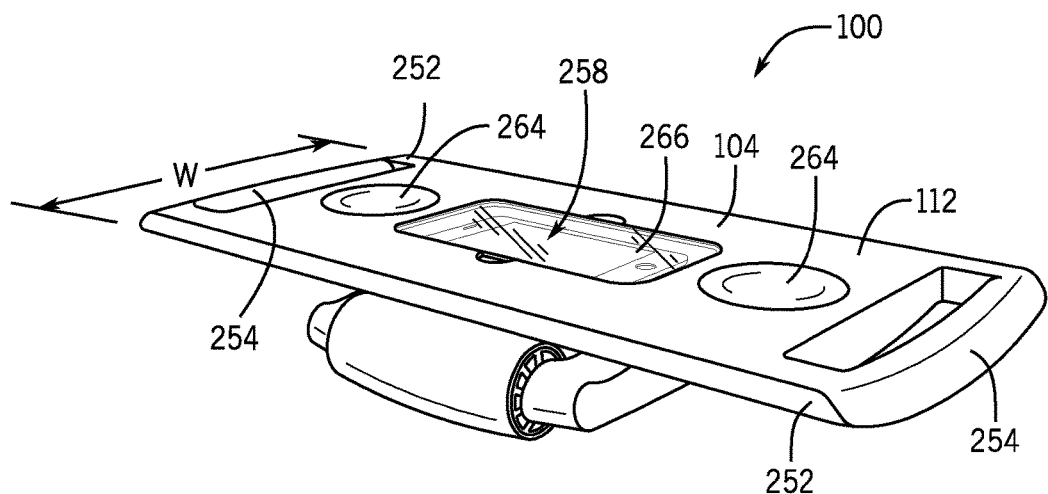
FIG. 42 is a perspective view of an additional embodiment of the fitness training device including a compartment for receiving a sensing device.
Figure 43:
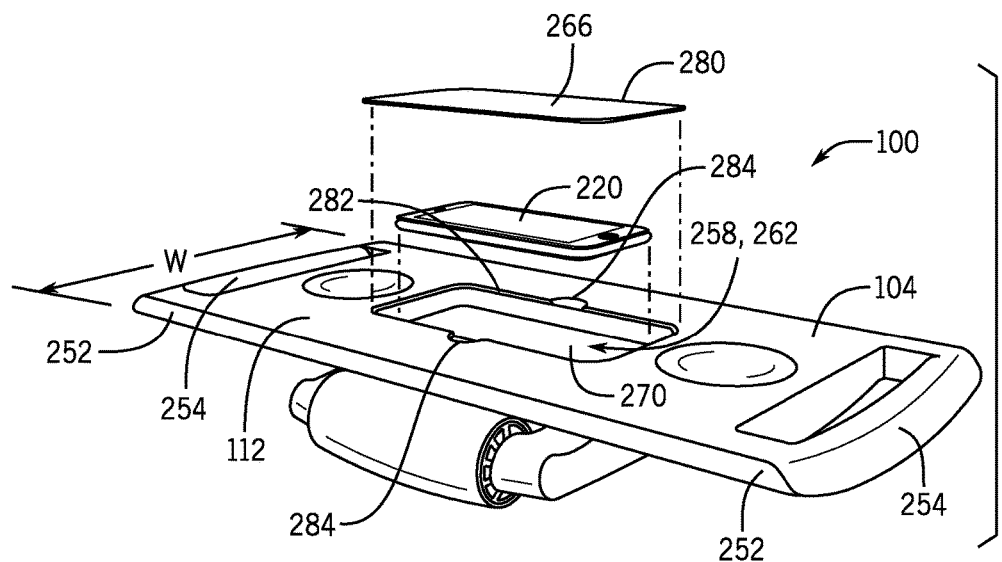
FIG. 43 is a partially exploded view of the fitness training device of FIG. 42.

An alternative design for a comfortable hand support in various embodiments may include integration of handles 254 into opposing ends (e.g., the end caps 252) of the deck 104 (see FIGS. 42 and 43). For example, the handles 254 may be integrated into the end caps 252 such that the handles 254 extend along a portion of the width W of the deck 104. In some embodiments, the handles 254 may have a generally cylindrical or rod-like shape, and may be curved along their respective lengths, to provide a comfortable grip. Supporting one's body weight such as in a plank position makes an important case for a comfortable grip. Additionally or alternatively, a plurality of recesses 264 or depressions (e.g., two shallow recesses 264) may be added to the top of the deck pad 256, which may help the user to find the correct hand, foot, or heel position when performing a desired exercise (see FIG. 14). For example, the recesses 264 may provide tactile feedback for the hands, heels, and/or feet of the user to be quickly placed in a correct location. In the illustrated examples of FIG. 14 and FIGS. 42 and 43, the recesses 264 are round, although various shapes, for example oval or irregular, may be acceptable for the purposes provided.

Figure 44:
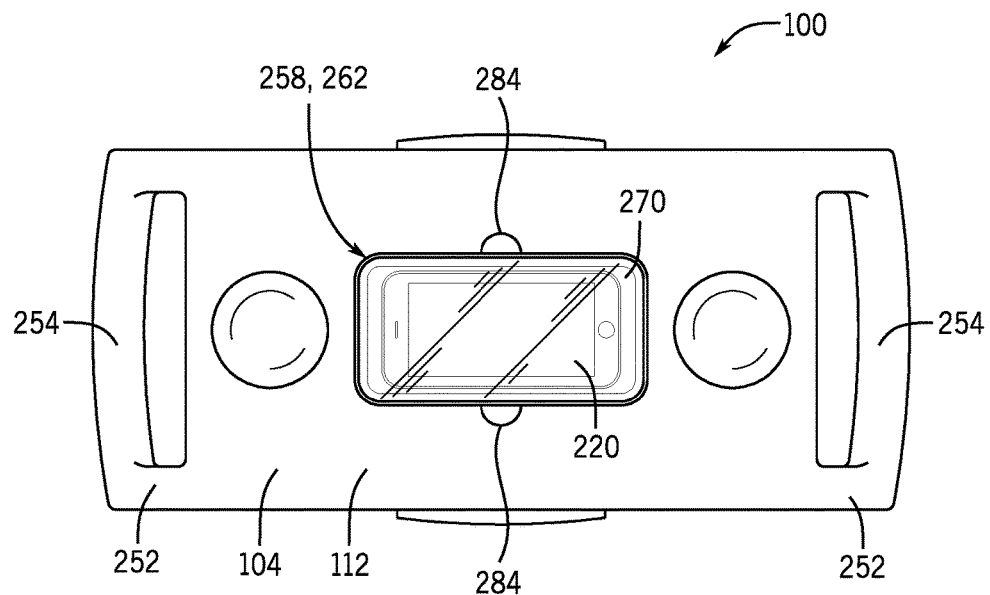
FIG. 44 is a top view of the fitness training device of FIG. 42.

With reference to FIGS. 42-44, in some embodiments, the fitness training device 100 may include a compartment 258 for receiving the sensing device 220 during use and/or storage of the fitness training device 100. In one embodiment, the compartment 258 may include a cavity 262 defined in the top surface 112 of the deck 104, such as between the plurality of recesses 264 and/or at or near the center of the deck 104. The cavity 262 is sized and shaped to receive the sensing device 220. For example, the cavity 262 may have a length greater than its width, and a width greater than the depth. In one embodiment, the compartment 258 may include a support pad 270 positioned within the cavity 262 to hold and support the sensing device 220. Like the mounting pad 232, the support pad 270 may be formed from silicone rubber and may be sticky or include a gripping feature. To protect the sensing device 220 during exercise and/or storage, the compartment 258 may include a cover member 266 operable to selectively cover the cavity 262 and enclose the sensing device 220 within the compartment 258. The cover 266 may be removably secured in place by a press-fit between the periphery 280 of the cover 266 into the periphery 282 of the cavity 262 (see FIG. 43), or it may be held in place by detents (protrusions and corresponding recess) formed in the sidewall of the cover 266 and the top rim of the cavity. As illustrated in FIG. 43, opposing depressions 284 may be located along the long side edges of the cavity 262 to allow a user to pry the cover 266 open to access the cavity 262. In some embodiments, the cover member 266 may be transparent or translucent to allow a user to view the sensing device 220 during exercise movements.

The fitness training device 100 may be formed from a variety of materials and means. For instance, in one or more examples of embodiments, the deck 104 may be formed of extruded aluminum material or other suitable material. The aluminum extrusion process may allow for design features to be integrated, such as screw bosses and the rib 160 for the wheel brackets 108. Alternative materials may be used for the deck 104, including plywood, injection-molded plastic, die-cast metal, or stamped metal. The wheel brackets 108 and the bracket 216 may be formed from any suitable material, including a thermoplastic material (self-reinforced or fiber reinforced), nylon, LDPE, ABS, polycarbonate, polypropylene, polystyrene, PVC, polyamide, and/or PTFE, among others, and may be formed or molded in any suitable manner such as by plug molding, blow molding, injection molding, extrusion, or the like.

In general, a user may engage the fitness training device 100 with an appropriate portion of the body for accomplishing a desired exercise. For example, the user may place one foot or both feet on the deck 104, or may grip the deck 104 with the user's hands. The user may then move the fitness training device 100 in a desired direction. The convex shape of the wheels 192 (e.g., the wheel tread 204), as well as the front-to-back tilting permitted by the wheel brackets 108, may allow the deck 104 to be balanced and steered into broad arcing turns, which may enable a broader range of movements.

Figure 24:
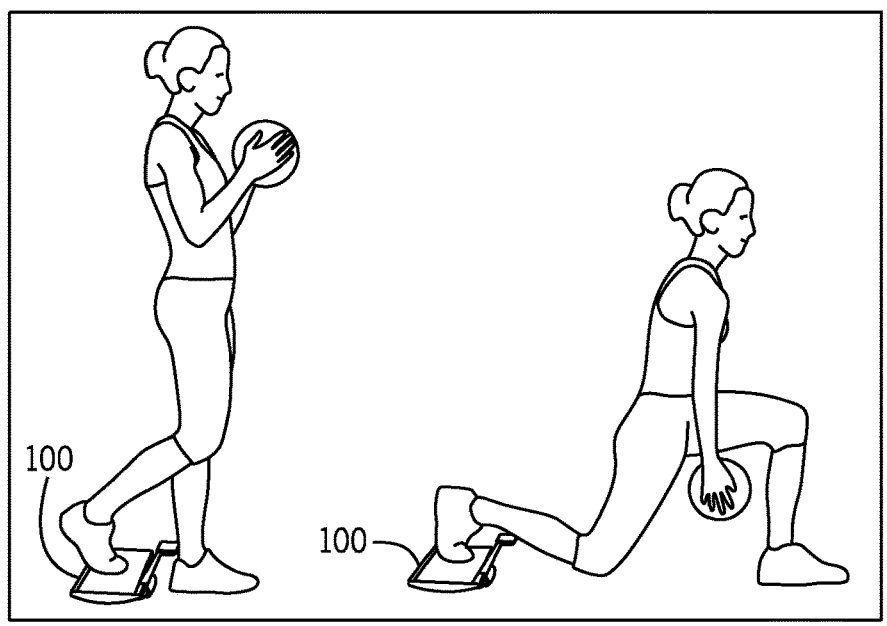
FIG. 24 shows a user using the fitness training device to perform a rear lunge exercise.
Figure 25:
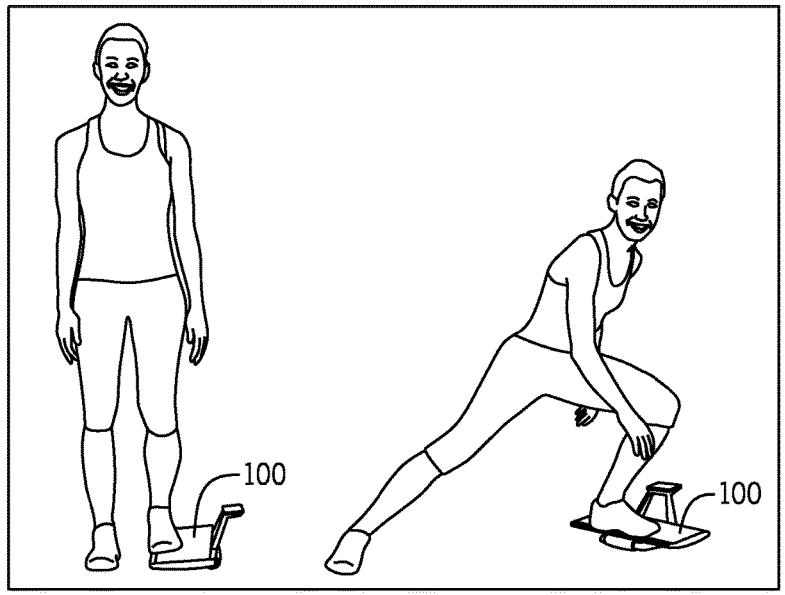
FIG. 25 shows a user using the fitness training device to perform a side lunge exercise.
Figure 26:
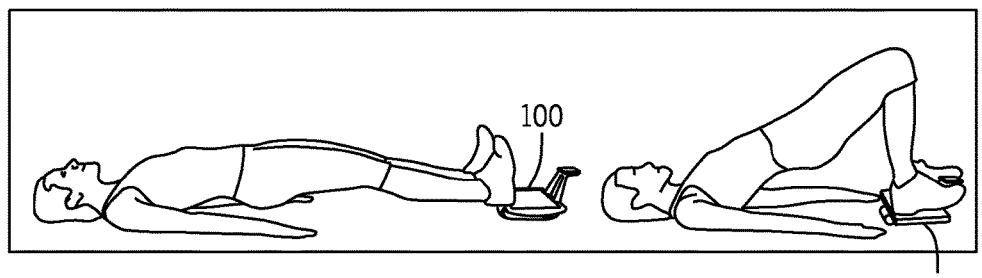
FIG. 26 shows a user using the fitness training device to perform a hamstring curl exercise.
Figure 27:
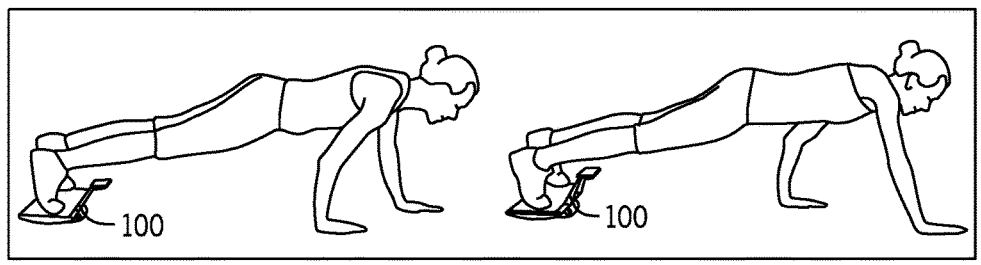
FIG. 27 shows a user using the fitness training device to perform a reptilian crawl exercise.
Figure 28:
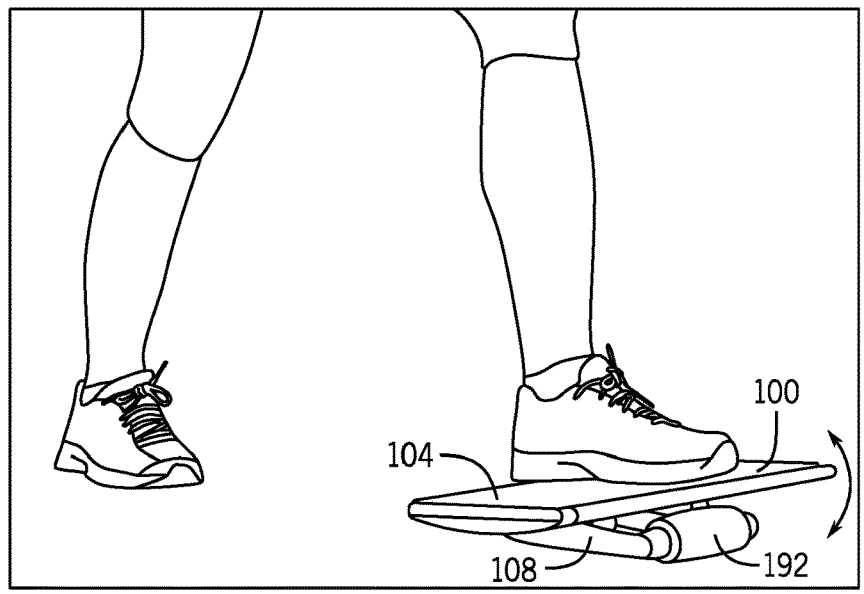
FIG. 28 is an enlarged view of a user activating a braking function of the fitness training device.
Figure 29:
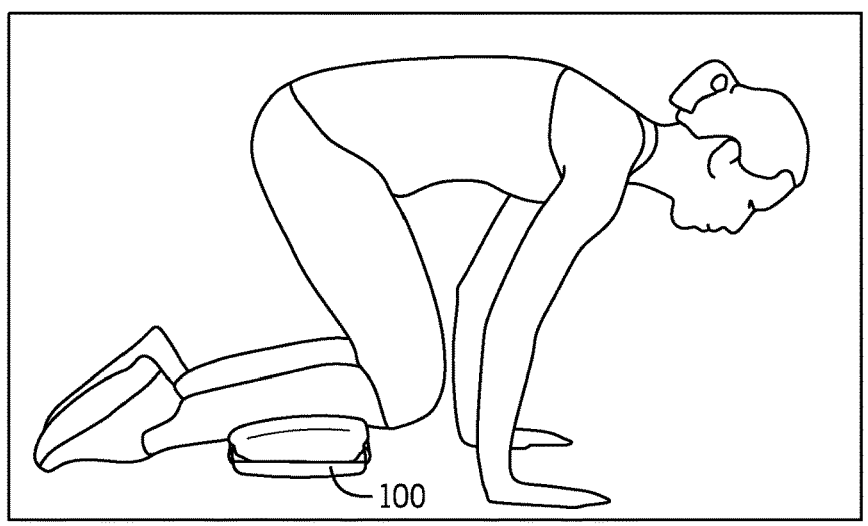
FIG. 29 shows an additional method of interfacing with the fitness training device.

Various exercises may be accomplished using the fitness training device 100. As indicated, a user can accomplish a broad range of exercises such as lunges, abdominal extensions, atomic pushups, hamstring curls, reptilian crawls, pike ups, and several others with this single device. Examples of various exercises to be accomplished are shown in FIGS. 20-29. Many variations of these moves are possible. For example, one may place the lower legs instead of the toes or feet on the deck 104 (see FIG. 29), or the forearms instead of the hands on the deck 104. Both of these variations reduce the cantilever of the body's weight, thus making the exercise easier. Conversely, exercises such as lunges may be made more challenging by holding weights such as dumbbells or a medicine ball as shown in FIG. 24.

During operation, the user may execute a braking function or action to slow down or stop the fitness training device 100 from rolling. The method for braking may be simple and intuitive for a user, and may involve angling (or edging) the deck 104, rotating the deck 104 about 5 to 10 degrees (e.g., about 7 degrees) in reference to the floor and with reference to a side plane (see FIG. 28). The edging movement may be accomplished by bringing the bottom surface 116 of the deck 104 in contact with the wheel 192 (e.g., within the recess portions 212), to create friction with the wheel 192 and cause the wheel 192 to slow down or stop rotating. As noted above, the damping members 184 may keep the deck 104 positioned away from the wheels 192 so that some amount of force is required to angle the deck 104 and create the braking effect. For example, the damping members 184 may provide a resilient pushback or return force when the user engages in an off-center, angled load on the deck 104 with reference to the side plane. There may be a number of possible variations to execute this feature. For instance, if one wanted to create a faster brake effect, an intermediary rubber pad could be added between the wheel 192 and the bottom surface 116 of the deck 104 (e.g., within the recess portions 212) to increase the friction and stopping power, or the surface of the recess portions 212 may be formed with ribs or other surface features, to enhance the friction force applied to the wheel 192 during breaking. Conversely, to reduce the braking force, a low friction intermediary material, such as nylon, Teflon®, or other, could be added.

This design may be modified in many ways. For instance, the deck 104 could be supported by four wheels 192 instead of two as shown in the illustrated embodiments. In one example, if the four wheels are close enough together and the geometry of the wheel designed correctly, a four-wheeled example may provide the angular rocking as well as the ability to steer the deck 104 into doing turns. In some embodiments, the fitness training device 100 may include more than two wheels 192 to provide different tilting and thus balance training characteristics. Compressible rubber pads may be shown in the various figures as the method in which the wheel brackets 108 are dampened; however, there are many other ways in which this same feature can be executed, such as compression springs, extension springs, leaf springs, or other methods to create resistance. The damping members 184, including any compression pads, can be interchangeable to allow for a range of resistances. For instance, an adult using the fitness training device 100 may want more resistive force than a child. Another option is that the damping members 184 could be tightened or loosened to allow adjustability to the resistance provided by the damping members 184. There are other compression and braking methods not mentioned here; however, all or many may accomplish the same end purpose of dampening the rocking of the deck 104 and bringing the deck 104 to a stop.

In various embodiments, the fitness training device 100 may include fitness training software 268 to track the user's movement using the sensing device 220 for reporting to a server or reflecting upon a user interface. For example, as a user shifts weight one direction to another, a sensor such as a gyroscope or accelerometer may detect the movement from one side to another and provide the individual with feedback.

The training software 268 may operate as a cloud-based system provided on a smartphone; however, the data can also be transmitted to a tablet or a computer. In alternative embodiments, the software 268 may be a device-native application having cloud storage components. In various embodiments, the software 268 may require interfacing with a number of network protocols, including Bluetooth for device-to-device communication and Wi-Fi or cellular Internet for storage of data on a server. In various embodiments, the software 268 may allow for storage of data in the memory of the device itself.

Figure 39:
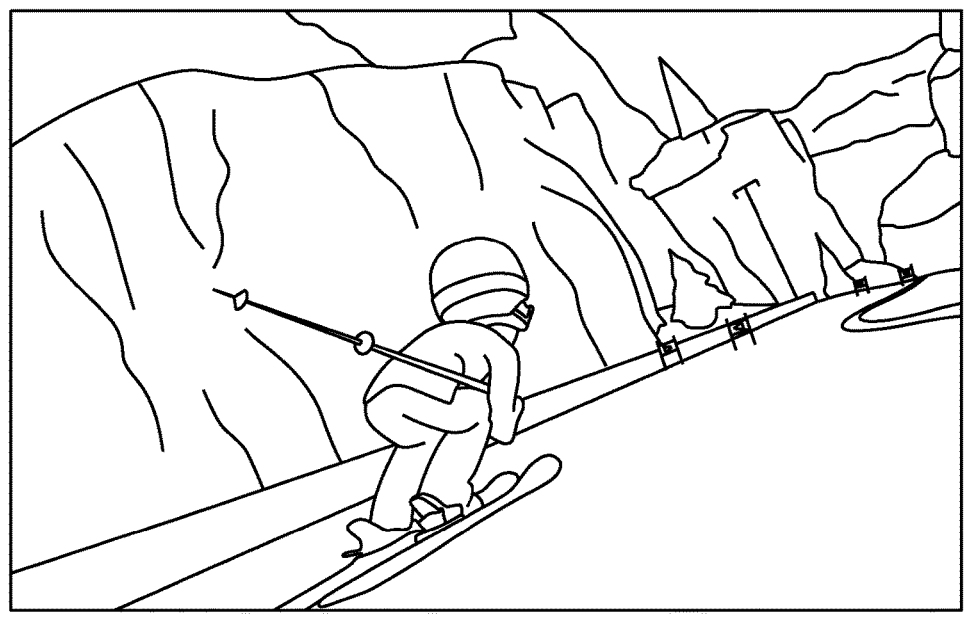
FIG. 39 shows an example of a fitness game.
Figure 40:
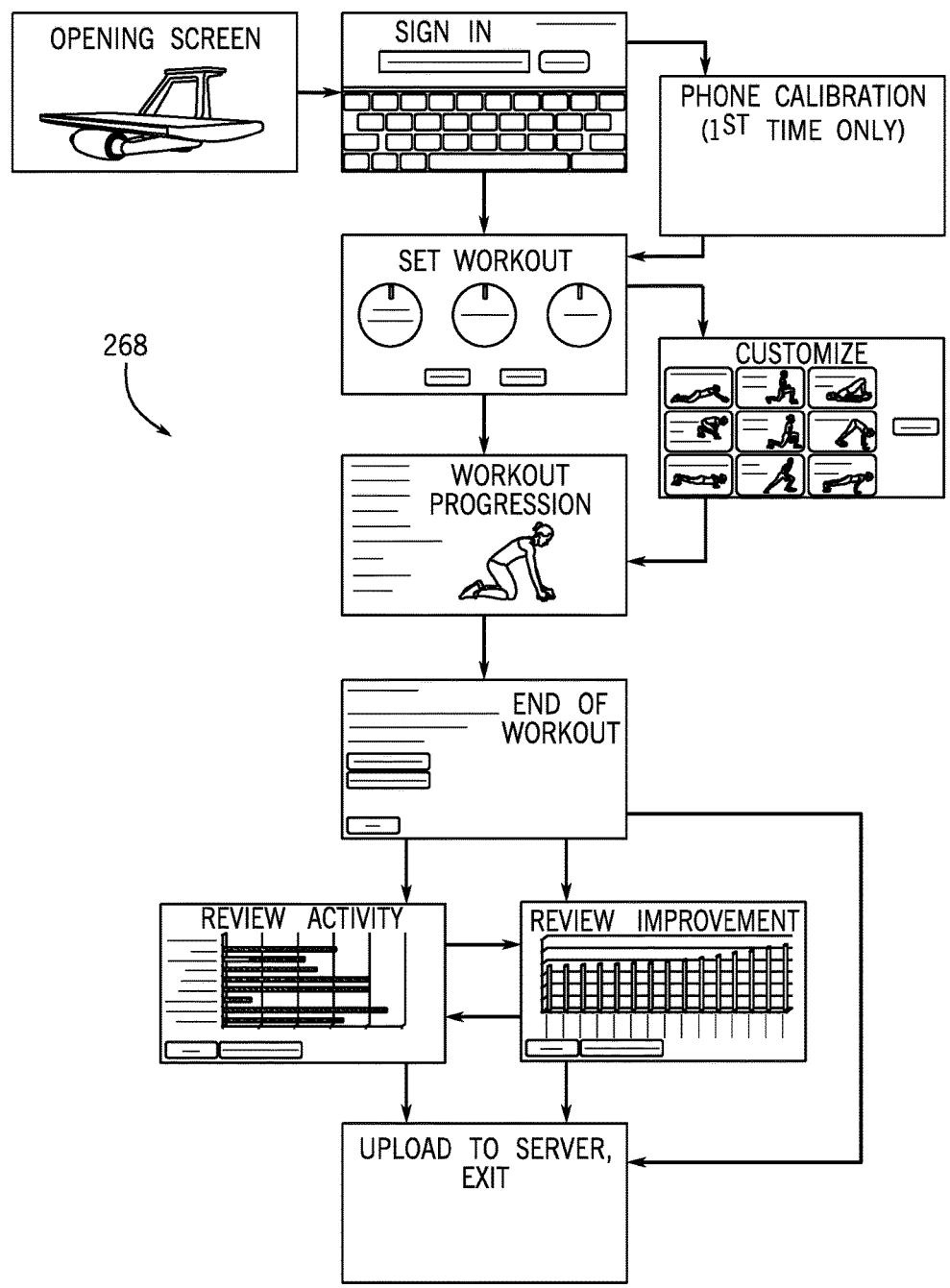
FIG. 40 is a schematic diagram of the fitness training software.

To allow use in medical environments, the software 268 can be set up in a HIPAA-compliant backend system. For example Amazon Web Services may be used. The software 268 and fitness training device 100 may allow the user to potentially share data with their physical therapist for monitoring progress in a recovery program. The data can also be shared with a trainer or coach, for guidance on improvement, or even real-time coaching from a remote location. Or, the data can be shared with friends and family, for fun or for competitive purposes. The training software 268 can be expanded to include more game-like exercises, with the roller board effectively operating as a new type of game controller (see FIG. 39).

Figure 33:
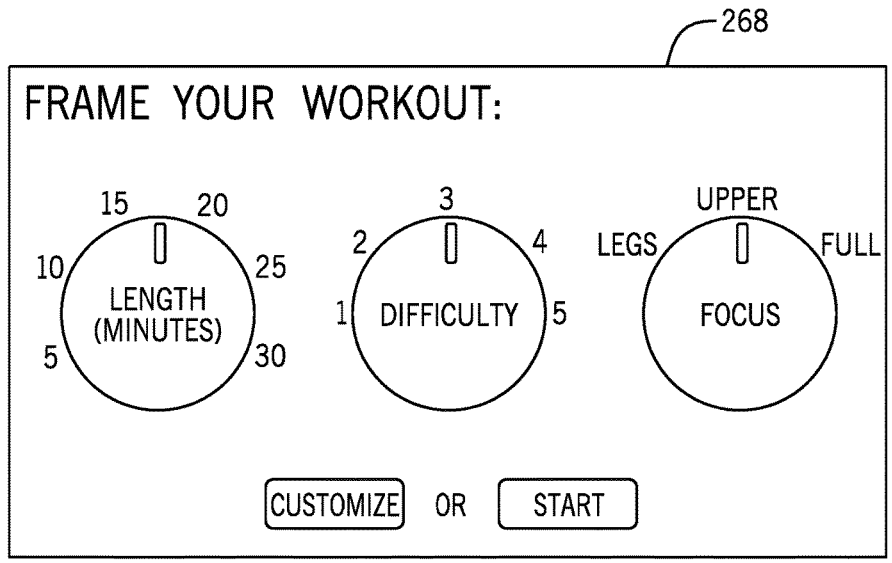
Figure 34:
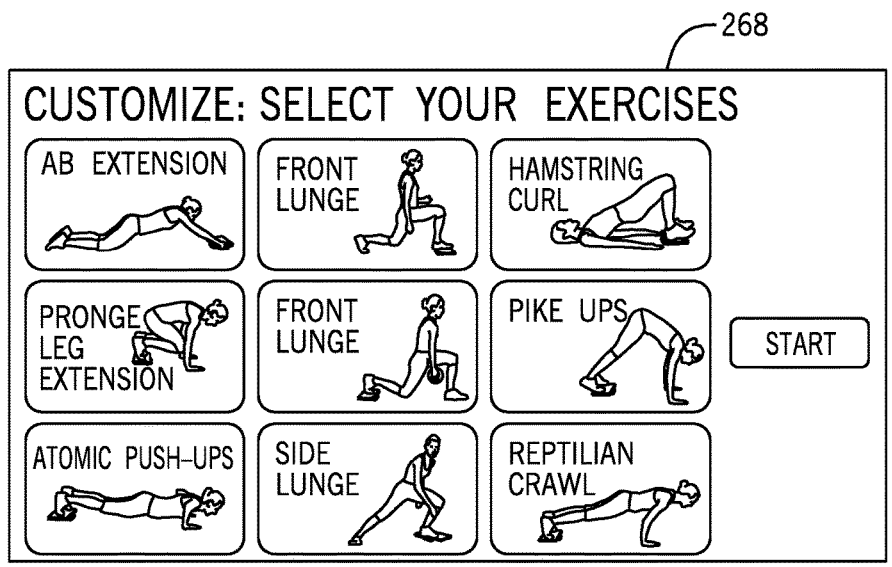
Figure 35:
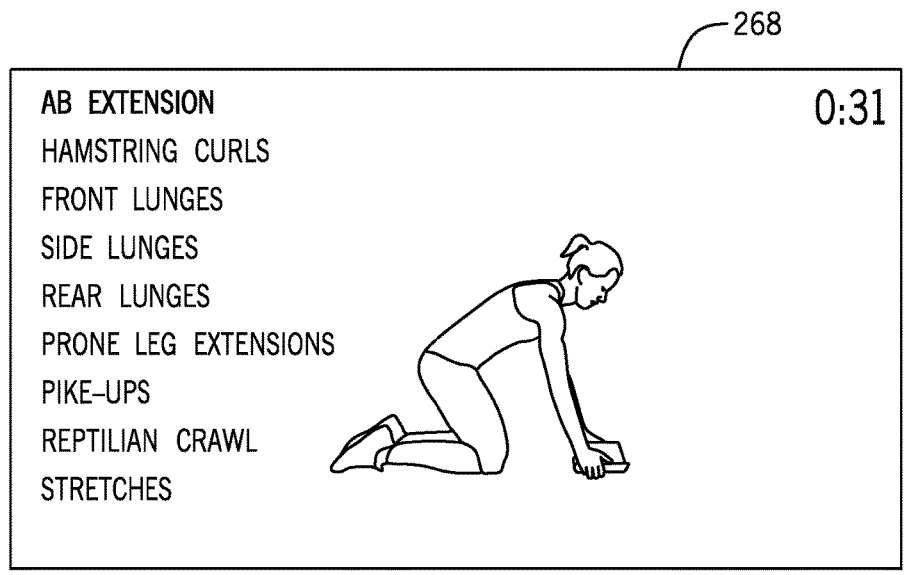

In the examples shown (e.g., FIGS. 31-38, FIG. 40), users may open the app on their smartphone, sign in using their email, Facebook, Twitter or LinkedIn account, then set up the type of workout they'd like to do. The software 268 may allow the user to adjust the length of the workout, the difficulty of the workout, and what part(s) of the body they want to focus on (see FIG. 33). The program may create the workout based on this input, or the user may have the option to customize the workout further by selecting the specific exercises (see FIG. 34). A typical workout may involve having a total of around six different exercises, and it may last an average of around 20 minutes. The software 268 may allow the number of exercises, the intensity, and the total time to be increased or decreased. As a workout history is established, the software 268 may start to suggest more challenging variations. One example of the graphic layout of the video display for each exercise consists of a view of the trainer in the center of the screen performing the exercise, a countdown timer in the upper right corner which counts the number of seconds remaining with that particular exercise, and along the left is a column listing all the different exercises to be performed in the workout, with the current exercises highlighted (see FIG. 35). Another option is to have a "calorie counter" in the lower right corner.

In addition to the visual feedback, the software 268 may allow for audio feedback. A tone may indicate the start of each extension, and a second, different tone may indicate the end of the extension. This would eliminate the need to be always watching the screen in order to stay in sync with the trainer. The software 268 may provide for a countdown to the start of the exercise (e.g., "OK, ready, set, go . . . ") and at the end (e.g., "three more, two more, last one . . . "). Because the movements in the workout are being tracked by the sensors in the smartphone, the software 268 (e.g., commentary) can also provide customized feedback. For instance, if the user starts to slow down towards the end, the software 268 (e.g., commentary) may provide encouragement (e.g., "This is a hard exercise but you're doing great. Try to keep up for just five more reps!"). The software 268 may provide the user with the option of turning the commentary on or off.

Figure 36:
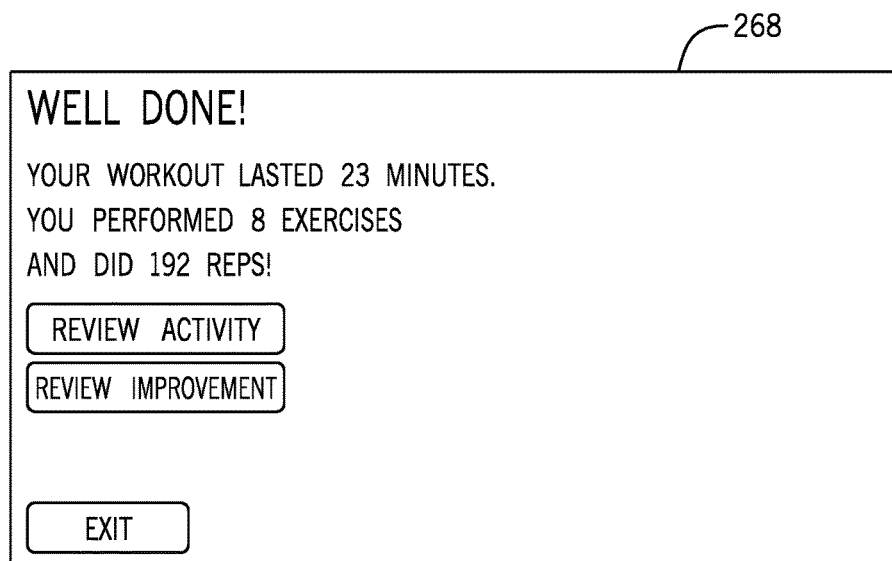
Figure 37:
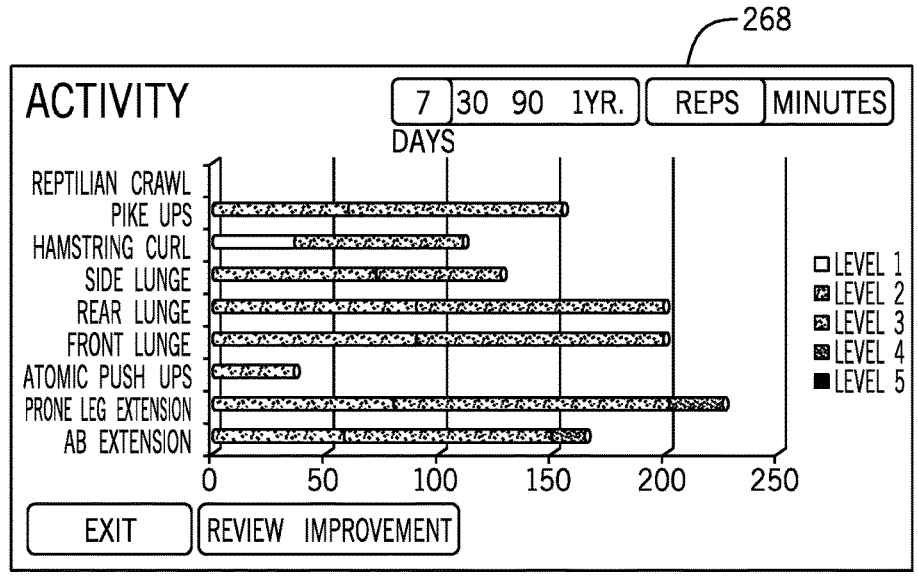
Figure 38:
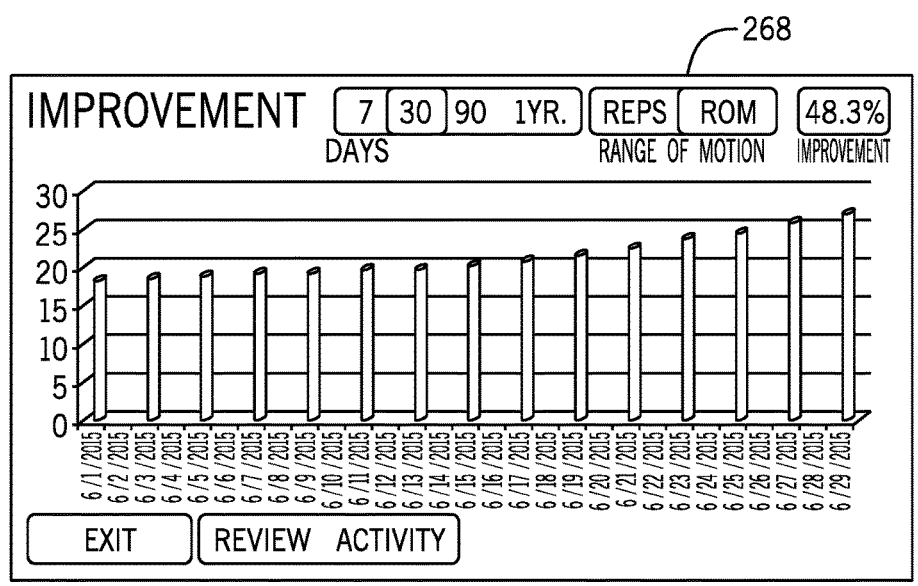

Referring to FIGS. 36-38, at the end of the workout, the software 268 may be configured to provide encouragement and a brief overview of the user's performance. The user may also choose to review stats of their ability (see FIG. 37), and their improvement over time (see FIG. 38). As a result of data collection and aggregation by the application, the user may be able to see their improvement in their exercises or number of repetitions over time. Data collected by sensors provided in the sensing device 220 attached to the fitness training device 100 may allow for the determination of distance of the system travelled and degree of linear or non-linear motion, which may be extrapolated into repetition of movement. For example, if the exercise requires execution of an arcing turn (see, e.g., FIG. 30), the system may measure the arc of the turn for its calculation of feedback. The sensors may continually monitor this information to give feedback, in various embodiments, at a constant rate, to the user as exercises are performed. The constant monitoring may allow for the reflection of the number of repetitions by the system to the user, such as a display of the number of times an exercise is performed or audio reflection of the number of repetitions left. For example, the sensors may measure arcing turns using suitable sensor means. These may include, for example, comparing location information obtained via GPS or Wi-Fi. The sensors may allow or determine how fast, far, and what direction the fitness device or board is travelling or has travelled.

The software 268 may be tailored specifically to provide for movements specific to the fitness training device 100 disclosed herein. Therefore, the cycle of sensor data and determination may be custom configured to function specifically with the device, and may be tailored to the device and its holder parameters.

The sensing device and fitness training device 100 may be supplemented by a secondary screen or display 272 (see FIG. 19), which may be mounted on a stand 274. In various embodiments, the secondary screen or display 272 may mirror a display provided on the sensing device 220 (for example, a phone screen if the device is a smartphone). The sensing device 220 may send a display signal to a number of compatible secondary screens or displays 272. The secondary screen or display 272 may include a tablet, laptop, TV (by way of a data receiving device, such as a Roku, Apple TV, or any similarly functional device which outputs to a supplemental screen for display of a video signal). Similarly, such a receiving device may be embedded in the screen. The video signal may be sent via a number of data transmission protocols, including, but not limited to, Bluetooth or other radio signal, Wi-Fi, or other data transmission means. The secondary display or screen 272 may accept input or be passive recipient of display data. For example, if the secondary display or screen 272 is a smart device, such as a tablet or laptop, the device may be used to operate the training software 268. A smart device may be defined as a device that allows for inputs and operation of the software 268 provided herein. In various embodiments, the secondary display or screen 272 may allow for installation of the software 268 described herein—in other words, the secondary display or screen 272 may also operate a version of the fitness software 268, wherein inputs may be transferred from the primary sensor device.

As an example data flow, the sensing device 220 may be provided in (see FIGS. 42 and 43) or attached to (see FIG. 3) the fitness training device 100. When a user begins a workout, the user may launch the application (or fitness software 268) on the sensing device 220, which may begin detecting movements of the fitness training device 100. The user may choose to see the workout process on a secondary display or screen 272. To enable this functionality, a user may turn on the secondary display or screen 272, and depending on the type of secondary screen—for example, if the secondary display or screen 272 is a tablet or laptop—launch a version of the fitness application provided thereon. As the user performs exercises using the fitness training device 100, the sensing device 220 may detect movements and update not only a screen which may be provided on the sensing device 220 but also on the secondary display or screen 272. Updates may be transmitted and reflected on the secondary display or screen 272 continuously, for example, as long as the application is active. Updating the screen may be facilitated through, among other methods, wireless transmission mechanisms, facilitating continual communication between the sensor devices and display devices.

The sensing device 220 may, as described previously, be a smartphone. For example, the smartphone may be, in various embodiments, an Android or iPhone device (or a suitable device running an Apple mobile operating system). The fitness software 268 may be game-like. The software 268 may allow for access to onboard sensors—in various embodiments, using means provided within the device and operating system. For example, the software 268 may be created using a platform suitable across devices, such as the Unity 3d game platform for the front-end interface. For an Apple device, objective C may be used along with Apple internal functionality to access acceleration and motion in all three dimensions. For an Android device, the sensor object may be used using Java to gain access to acceleration and motion. The values of these readings may be stored in an external storage location such as, but not limited to, a cloud server as described above. Stored data may be used to generate analytics and comparison data. The data may be calculated based on variables such as age, sex, and weight. Variable data may be inputted by a user during, for example, software configuration.

In one or more example embodiments, in operation, the software 268 may initiate measurement during a user session. A user may choose to launch the software 268, a countdown timer may be shown to the user, and at the end of the timer the game or exercise video may begin along with the querying of sensors or other mechanism for capturing measurements. During the session, motion and distance data may be collected regularly, for example 45 times every second. Real-time analysis may be performed based on arc, motion and timing to determine if the user is successfully completing the exercise that they selected. Arc, motion, and timing information may be determined using a combination of data provided by the sensing device 220. The user session may end based on pre-configured parameters, for example, the time that was input by the user before the session starts.

As utilized herein, the terms "approximately," "about," "substantially", and similar terms are intended to have a broad meaning in harmony with the common and accepted usage by those of ordinary skill in the art to which the subject matter of this disclosure pertains. These terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the subject matter as recited in the appended claims.

References to relative positions (e.g., "top" and "bottom") in this description are merely used to identify various elements as are oriented in the figures. The orientation of particular components may vary greatly depending on the application in which they are used.

The term "coupled" means the joining of two members directly or indirectly to one another. Such joining may be stationary in nature or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

The construction and arrangement of the system, methods, and devices as shown in the various examples of embodiments is illustrative only. Although only a few embodiments have been described in detail, those skilled in the art will readily appreciate that many modifications are possible (e.g., variations in sizes, dimensions, structures, shapes and proportions of the various elements, values of parameters, mounting arrangements, use of materials, colors, orientations, etc.) without materially departing from the teachings and advantages of the subject matter recited. For example, elements shown as integrally formed may be constructed of multiple parts or elements, the operation of the interfaces may be reversed or otherwise varied, the length or width of the structures and/or members or connector or other elements of the system may be varied, the nature or number of adjustment positions provided between the elements may be varied. The order or sequence of any process or method steps may be varied or re-sequenced according to alternative embodiments. Other substitutions, modifications, changes and omissions may be made in the design, operating conditions and arrangement of the various examples of embodiments without departing from the spirit or scope of the subject matter described herein.

While the fitness training device 100 has been described in conjunction with the examples of embodiments outlined above, various alternatives, modifications, variations, improvements and/or substantial equivalents, whether known or that are or may be presently foreseen, may become apparent to those having at least ordinary skill in the art. Accordingly, the examples of embodiments of the fitness training device 100, as set forth above, are intended to be illustrative, not limiting.

What is claimed is:

1. A fitness training device, comprising:
   a deck comprising a top surface, a bottom surface, and opposing first and second side edges and opposing front and rear longitudinal edges together forming a perimeter of the deck;
   a wheel bracket structure positioned below the deck, the wheel bracket structure rotatably supporting first and second rollers and pivotally coupled to the deck about a pivot line extending between the opposing first and second side edges of the deck; and
   a resilient member connected to the wheel bracket structure and the deck;
   wherein:
   each of the first and second rollers has a maximum diameter that is less than its overall length;
   the bottom surface includes a recess portion sized for receipt of a peripheral portion of the first and second rollers; and
   relative movement between the deck and the wheel bracket structure causes contact between the recess portion and a peripheral portion of the first and second rollers to create a braking action.

2. The fitness training device of claim 1, wherein the first and second rollers are positioned to rotate about an axis parallel to the pivot line.

3. The fitness training device of claim 1, wherein each of the first and second rollers includes a varying diameter that increases along the length of the roller from opposing ends of the roller towards a mid-point of the roller.

4. The fitness training device of claim 1, wherein each of the first and second rollers includes a convex outer surface that allows the deck to rock along a length dimension of the deck extending between the first and second side edges to provide lateral instability.

5. The fitness training device of claim 4, wherein:
   the first and second rollers each include a central longitudinal axis oriented parallel to the pivot line; and
   the first and second rollers are offset from the pivot line in opposite directions along a width dimension of the deck extending between the front and rear longitudinal edges.

6. The fitness training device of claim 1, wherein each of the first and second rollers is positioned so that at least 50% of the maximum diameter is within the perimeter of the deck.

7. The fitness training device of claim 1, wherein the resilient member is received at least partially within a cavity defined in an upper surface of the wheel bracket structure and is configured to contact the bottom surface of the deck.

8. The fitness training device of claim 1, wherein:
   the deck includes a channel extending at least partially along the bottom surface between the opposing first and second longitudinal side ends;
   the wheel bracket structure includes a securement structure; and
   further comprising a joint formed by the securement structure positioned within the channel and defining the pivot line, the joint accommodating relative movement between the deck and the wheel bracket structure.

9. The fitness training device of claim 8, wherein the relative movement between the deck and the wheel bracket structure is resisted or dampened by the resilient member.

10. The fitness training device of claim 8, wherein:
    the channel is C-shaped and includes first and second troughs and a rib having a convex lower surface;
    the securement structure is C-shaped and includes a first portion and a second portion, the second portion having a concave upper surface; and
    the concave upper surface of the securement structure engages the convex lower surface of the rib to define the pivot line.

11. The fitness training device of claim 10, wherein:
    the second portion of the securement structure includes opposing arms extending away from each other; and
    the opposing arms are each received in an adjacent one of the first and second troughs.

12. The fitness training device of claim 11, wherein:
    the channel defines a gap including a first width dimension;
    the opposing arms define a second width dimension; and
    the first width dimension is less than the second width dimension to retain the second portion of the securement structure within the channel.

13. The fitness training device of claim 1, wherein:
    the wheel bracket structure includes first and second wheel brackets; and
    each wheel bracket is positioned adjacent one of the opposing first and second side edges and perpendicular to a width of the deck.

14. The fitness training device of claim 13, wherein:
    the deck includes a channel extending along the bottom surface between the opposing first and second longitudinal side ends;
    each wheel bracket includes a securement structure; and
    further comprising a joint formed by an engagement of the securement structure on each wheel bracket and the channel, each joint defining a common pivot line, the joint accommodating relative movement between the deck and the wheel bracket structure.

15. The fitness training device of claim 14, wherein the relative movement between the deck and the wheel bracket structure is resisted or dampened by the resilient member.

16. The fitness training device of claim 1, further comprising a deck pad positioned on the top surface of the deck.

17. The fitness training device of claim 16, wherein the deck pad includes depressions to provide tactile feedback for feet of a user to be quickly placed in a correct location.

18. The fitness training device of claim 1, wherein the materials and shapes of the top surface of the deck are configured to support hands of a user during exercises.

19. The fitness training device of claim 1, wherein the first and second rollers are barrel-shaped to allow the deck to rock slightly along a length of the deck, to move in broad arcing turns, or both.

20. The fitness training device of claim 1, wherein the deck can is configured to create a braking action when angled slightly towards and contacting one of the first and second rollers.

21. The fitness training device of claim 1, wherein the resilient member is operable to maintain the top surface of the deck substantially parallel to a support surface, and provides a resilient force when a user engages in an off-center, angled load on the deck with reference to a side plane.

22. The fitness training device of claim 1, wherein the first and second rollers are positioned so as to not extend beyond a peripheral edge of the deck.

23. A system including the fitness training device of claim 1, further comprising:
- a sensing device including a plurality of sensors and a primary display;
- a software provided on the sensing device; and
- a secondary display, wherein:
- the software enables periodic reading of the plurality of sensors to provide feedback to a user during a workout; and
- the software instructs the sensing device to transmit data to the secondary display.

* * * * *